(12) United States Patent
Barenholz et al.

(10) Patent No.: US 7,744,920 B2
(45) Date of Patent: Jun. 29, 2010

(54) USE OF LIPOSOMAL GLUCOCORTICOIDS FOR TREATING INFLAMMATORY STATES

(75) Inventors: Yechezkel Barenholz, Jerusalem (IL); Yaakov Naparstek, Jerusalem (IL); Yuval Avnir, Jerusalem (IL); Rina Ulmansky, Mevasseret Zion (IL)

(73) Assignees: Hadasit Medical Research Services & Development Limited, Jerusalem (IL); Yissum Research Development Company of the Hebrew University, Jerusalem (IL)

( * ) Notice: Subject to any disclaimer, the term of this patent is extended or adjusted under 35 U.S.C. 154(b) by 566 days.

(21) Appl. No.: 11/662,174

(22) PCT Filed: Sep. 11, 2005

(86) PCT No.: PCT/IL2005/000962
§ 371 (c)(1),
(2), (4) Date: May 1, 2007

(87) PCT Pub. No.: WO2006/027786
PCT Pub. Date: Mar. 16, 2006

(65) Prior Publication Data
US 2008/0003276 A1    Jan. 3, 2008

Related U.S. Application Data

(60) Provisional application No. 60/608,140, filed on Sep. 9, 2004.

(51) Int. Cl.
*A61K 9/127*    (2006.01)
*A61K 31/56*    (2006.01)

(52) U.S. Cl. .................................... 424/450; 514/169
(58) Field of Classification Search .................. None
See application file for complete search history.

(56) References Cited

FOREIGN PATENT DOCUMENTS

| DE | 19607722 A1 | * | 9/1997 |
| DE | 10255106 A1 | * | 6/2004 |
| WO | WO 2004047792 A2 | * | 6/2004 |

OTHER PUBLICATIONS

Fildes, et al. (1978) Journal of Pharmacy and Pharmacology, 30(6): 337-42.*
Schmidt, et al. (2003) 126: 1895-1904.*
Gonzalez-Rothi, et al. (1996) Pharmaceutical Research, 13(11): 1699-1703.*
Metselaar, et al. (2003) Arthritis & Rheumatism, 48(7): 2059-66.*
Lopez-Garcia, et al. (1993): 45(6): 576-78.*
Metselaar, et al. (2002) Cell. Mol. Biol. Lett., 7(2): 291-92.*
Love, et al. (1990) Annals of Rheumatic Diseases, 49: 611-14.*
Metselaar, et al. (2004) Ann. Rheum. Dis., 63: 348-53.*
Mishina, et al. (1996) Pharmaceutical Research, 13(1): 141-45.*

* cited by examiner

*Primary Examiner*—Robert M Kelly
(74) *Attorney, Agent, or Firm*—The Nath Law Group; Suzanne M. Hopkins; Ari G. Zytcer

(57) ABSTRACT

The present invention provides the use of a glucocorticoid (GC) or of a GC derivative encapsulated in a liposome for the preparation of a pharmaceutical composition for the treatment of an inflammatory associated condition in a subject, provided that said condition is not associated with a neurodegenerative disease or disorder. A specific use concerns a liposomal formulation comprising methylprednisolone sodium hemisuccinate (MPS) for the treatment of rheumatoid arthritis.

16 Claims, 7 Drawing Sheets

USE OF LIPOSOMAL GLUCOCORTICOIDS FOR TREATING INFLAMMATORY STATES

CROSS-REFERENCE

This is a National Phase Application filed under 35 U.S.C. 371 of International Application No. PCT/IL2005/000962, filed Sep. 11, 2005, claiming the benefit under 35 USC 119(e) of U.S. Provisional Application No. 60/608,140, filed Sep. 9, 2004, the entire contents of each of which is hereby incorporated herein by reference in its entirety.

FIELD OF THE INVENTION

This invention relates in general to liposome technology, and specifically, to the use of this technology the delivery of glucocorticoids.

LIST OF PRIOR ART

The following is a list of prior art which is considered to be pertinent for describing the state of the art in the field of the invention.

Gonzalez-Rothi, Ricardo J et al. *Pharmaceutical Research* 13(11): 1699-1703 (1996);
Schmidt J et al. *Brain* 126(8):1895-1904 (2003);
Fildes F J et al. *J Pharm. Pharmacol.* 30(6):337-42 (1978);
Mishina E V et al. *Pharm Res* 13(1):141-5 (1996);
Gonzalez-Rothi, Ricardo J et al. *Pharmaceutical Research* 13(11):1699-1703 (1996);
Metselaar J M, et al. *Ann Rheum Dis.* 63(4):348-53 (2004);
Metselaar J M, et al. *Arthritis Rheum.* 48(7):2059-66 (2003);
Metselaar J M, et al. *Cell Mol Biol Lett.* 7(2):291-2 (2002);
Lopez-Garcia F, et al. *J Pharm Pharmacol.* 45(6):576-8 (1993);
Love W G, et al. *Ann Rheum Dis.* 49(8):611-4 (1990);
Josbert M. Metselaar, Liposomal targeting of glucocorticoids. A novel treatment approach for inflammatory disorders. chapter 7, pp 107-122, 2003 Ph.D. Thesis, Utrecht University, Faculty of Pharmaceutical Sciences, Faculty of Veterinary Medicine ISBN 90-393-3285-1.

BACKGROUND OF THE INVENTION

Glucocorticoids (glucocorticosteroids) are a class of steroid hormones characterized by an ability to bind with the cortisol receptor found in the cells of almost all vertebrate tissues and trigger similar effects. Glucocorticoids are distinguished from other steroids such as sex steroids by the specific receptors, target cells, and effects. Cortisol (or hydrocortisone) is the most important natural human glucocorticoid.

Glucocorticoids have potent anti-inflammatory and immunosuppressive properties. This is particularly evident when they administered at pharmacologic doses, but also is important in normal immune responses. As a consequence, glucocorticoids are widely used as drugs to treat inflammatory conditions such as arthritis or dermatitis, and as adjunction therapy for conditions such as autoimmune diseases. On the other hand, excessive glucocorticoid levels result from administration as a drug or hyperadrenocorticism have effects on many systems, some examples including inhibition of bone formation, suppression of calcium absorption and delayed wound healing.

A variety of synthetic glucocorticoids, some far more potent than cortisol, have been developed for therapeutic use. They differ in the pharmacokinetics (absorption factor, half-life, volume of distribution, clearance) and in pharmacodynamics (for example the capacity of mineralocorticoid activity: retention of sodium ($Na^+$) and water). Because they absorb well through the intestines, they are primarily administered per os (by mouth), but also by other ways like topically on skin.

Methylprednisolone (pregna-1,4-diene-3,20-dione, 11,17,21-trihydroxy-6-methyl-,(6α, 11β). $C_{22}H_{30}O_5$, MW 374.48) is one example of a therapeutically potent synthetic glucocorticoid drug, which, due to its hydrophobic character, is usually taken orally. Like most adrenocortical steroids, methylprednisolone is typically used for its anti-inflammatory purposes. However, glucocorticoids have a wide range of effects, including changes to metabolism and immune responses. Similar to other corticosteroids, the list of diseases or pathological conditions for which methylprednisolone is effective is rather large. Common uses includes arthritis therapy, and short-term treatment of bronchial inflammation due to various respiratory diseases while highly effective, their systemic application is limited because of a high incidence of serious adverse effects, especially related to long-term treatment.

Efficacy and safety studies of systemic administration of glucocorticoids, revealed that in addition to the profound activity of the drug in many different tissues, these drugs have rapid clearance from plasma thereby requiring high and frequent dosing to obtain effective amounts at the target site.

Thus, alternative approaches for parenteral administration were investigated. For example, developing intralesional administration of glucocorticoids (e.g. by the use of inhalers in asthma and in intraarticular injection in arthritis) enabled the use of lower doses of the steroid while achieving sufficient drug levels in a lesion, with minimal side effects.

A further approach included targeting of the drug to the target tissue by the use of a suitable carrier, such as liposomes.

First attempts to encapsulate corticosteroids in liposomes was performed by Fildes F J et al. [J Pharm. Pharmacol. 30(6):337-42 (1978)] which included steroid encapsulation in the liposome's lipid bilayer. This approach was based on the understanding that corticosteroids are hydrophobic in nature. However, such liposomal formulations turned to be unsuitable for clinical applications.

Efforts were also made in developing "soluble" glucocorticoids. Examples include succinate derivatized steroids such as hydrocortisone hemisuccinate sodium salt and Methylprednisolone hemisuccinate sodium salt. Another group of soluble glucocorticoids include the phosphate derivatives of steroids. While rendering the steroid water soluble which enabled the use of the acidic steroids for injection, it was shown that these "pro-drugs" are completely cleared from plasma in less than 6 hours post injection. [Mishina E V et al *Pharm Res* 13(1):141-5 (1996)]

The combination of acidic steroids with liposomes was also investigated. Schmidt et al. [Schmidt J et al. *Brain* 126 (8):1895-1904 (2003)] describe a formulation of polyethyleneglycol (PEG)-coated long-circulating sterically stabilized liposomes encapsulating prednisolone phosphate (one of the water soluble pro-drug steroids) and its beneficial effect in treating multiple sclerosis as compared to the free form of the steroid. However, attempts to similarly encapsulate methylprednisolone hemisuccinate (a weak acid) failed, as it led to an unstable formulation.

Further, encapsulation in liposomes of triamcinolone acetonide phosphate, a water soluble strong acid derivative of triamcinolone (pKa below 2) was described [Gonzalez-Rothi, Ricardo J et al. *Pharmaceutical Research* 13(11):1699-1703 (1996)]. The liposomal formulation was prepared by passive loading of the acidic corticosteroid into the liposomes and used as an injectable dosage form (intravenous or intratracheal) for treating pulmonary conditions. Further, in ex vivo stability studies it was shown that after 24 hours the liposome retained more than 75% of the acidic corticosteroid.

SUMMARY OF THE INVENTION

The invention is based on the finding that using a chemically modified gluococorticoids (GC), to their amphipathic weak acid form stably loaded into liposomes, i.e. the majority of the substance remained within the liposome as intact acidic GC after storage for even 14 months at 4° C., were effective in ameliorating symptoms of rheumatoid arthritis in Adjuvant Arthritis (AA) induced animals.

Thus, according to a first of its aspects, the invention provides the use of a GC or GC derivative for the preparation of a pharmaceutical composition for the treatment of an inflammatory associated condition of a subject, provided that said condition is not associated with a neurodegenerative disease or disorder, said GC or GC derivative is encapsulated in a liposome and is essentially retained in said liposome for 6 months, the GC/GC derivative being selected from:
  i) an amphipathic weak base GC or GC derivative having a pKa equal or below 11 and a logD at pH 7 in the range between about −2.5 and about 1.5, preferably, in the range between about −1.5 and about 1.0;
  ii) an amphipathic weak acid GC or GC derivative having a pKa above 3.5 and a logD at pH 7 in the range between about −2.5 and about 1.5, preferably, in the range between about −1.5 and about 1.0.

The GC or GC derivative is preferably an acidic GC or GC derivative. When referring to a GC derivative, it is preferably an amphipathic weak acid derivative of GC which is converted to the non-acidic form upon release from the liposome to bodily fluids. More specifically, the acidic GC is methylprednisolone sodium hemisuccinate (MPS).

A preferred MPS formulation according to the invention comprises sterically stabilized liposomes (having a uniform size with an average diameter of about 80 nm) formed from a combination of hydrogenated soybean phosphatidylcholine (HSPC), polyethylene glycol coated distearoyl phosphatidyl ethanolamine (PEG-DSPE) and cholesterol at a mole ratio of 55:40:5.

The pharmaceutical composition is preferably utilized for the treatment or prevention of inflammation and autoimmune disorders, preferably for the treatment of autoimmune disorders, preferably, rheumatoid arthritis (RA).

Preferably the neurodegenerative disease excluded from the scope of the invention is multiple sclerosis.

Inflammation and Immune Responses

Immune processes are probably ongoing and, in most cases, lead to the elimination of antigens without producing clinically detectable inflammation. The development of clinically apparent inflammation indicates that the immune system has encountered either an unusually large amount of antigen, antigen in an unusual location, or antigen that is difficult to digest or that is processed in a way that results in an inflammation or an autoimmune disease. In some diseases, such as rheumatoid arthritis, the initiating agent is unknown or may be normal host tissue components. In others (e.g. systemic lupus erythematosus), inherent or acquired immunoregulatory abnormalities may contribute to the sustained nature of the inflammatory process.

Inflammatory responses and immune induced pathologies mediated by the immune system may be divided into four categories: I, II, III, and IV, which represent four distinct immune mechanisms.

I. Immediate hypersensitivity (allergic, or reaginic acute inflammation).
  II. Cytotoxic (inflammation mediated by cytotoxic antibodies).
  III. Immune complex (inflammation mediated by immune complex).
  IV. Delayed hypersensitivity (chronic inflammation mediated by lymphocytes and macrophages).

Each of the above mechanisms may result in the development of a medical condition associated with the immune system and which may be treated with the liposomal GC or GC derivative of the invention.

Thus, the invention also provides a method for the treatment of an inflammatory associated medical condition, provided that said condition is not associated with a neurodegenerative disease or disorder, the method comprising administering to a subject in need an amount of a GC or GC derivative encapsulated in a liposome and essentially retained in said liposome for 6 months, the amount being effective to treat said condition, wherein said GC or GC derivative is selected from:
  i) an amphipathic weak base GC or GC derivative having a pKa equal or below 11 and a logD at pH 7 in the range between about −2.5 and about 1.5, preferably, in the range between about −1.5 and about 1.0;
  ii) an amphipathic weak acid GC or GC derivative having a pKa above 3.5 and a logD at pH 7 in the range between about −2.5 and about 1.5, preferably, in the range between about −1.5 and about 1.0.

Yet further, the invention provides a pharmaceutical composition for the treatment of an inflammatory associated condition, the composition comprising an amount of a GC or GC derivative encapsulated in a liposome and retained in the liposome for 6 months, wherein the GC or GC derivative being selected from:
  i) an amphipathic weak base GC or GC derivative having a pKa equal or below 11 and a logD at pH 7 in the range between about −2.5 and about 1.5, preferably, in the range between about −1.5 and about 1.0;
  ii) an amphipathic weak acid GC or GC derivative having a pKa above 3.5 and a logD at pH 7 in the range between about −2.5 and about 1.5, preferably, in the range between about −1.5 and about 1.0.

Preferred conditions to be treated in accordance with the invention are inflammatory states affecting the joints or other organs, excluding the central nervous system, and/or inflammatory states responding or sensitive to GC treatment, excluding diseases of the CNS. A specific group of inflammatory states are the autoimmune conditions, specifically, Arthritis, more specifically, rheumatoid arthritis (RA).

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1A:
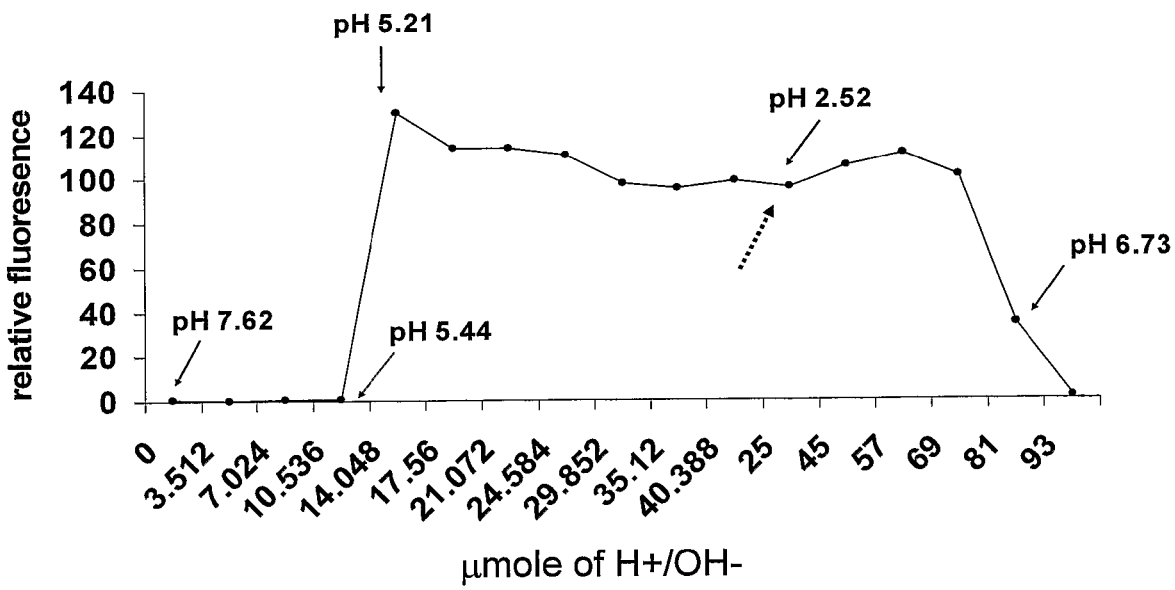
FIGS. 1A-1C are graphs showing chemical characteristics of methylprednisolone sodium hemisuccinate (MPS), including turbidity of MPS as function of pH (FIG. 1A); partition coefficient of MPS at different pH points (FIG. 1B); and surface tension of methylprednisolone hemisuccinate (MP-hemisuccinate) and dexamethasone phosphate (DEX-phosphate) as function of GC concentration (FIG. 1C).

Glucocorticoids (GCs) are a family of hormones that predominantly affects the metabolism of carbohydrates and, to a lesser extent, fats and proteins (and has other effects). Glucocorticoids are made in the outside portion (the cortex) of the adrenal gland and chemically classed as steroids. Cortisol is the major natural glucocorticoid. Nonetheless, the term glucocorticoid also applies to equivalent hormones synthesized in the laboratory.

A non-limiting list of glucocorticoids may be found at the internet site http://www.steraloids.com/, incorporated herein in its entirety by reference. Examples include prednisolone hemisuccinate, methylprednisolone hemisuccinate, dexamethasone hemisuccinate, allopregnanolone hemisuccinate; beclomethasone 21-hemisuccinate; betamethasone 21-hemisuccinate; boldenone hemisuccinate; prednisolone hemisuccinate, sodium salt; prednisolone 21-hemisuccinate; nandrolone hemisuccinate; 19-nortestosterone hemisuccinate; deoxycorticosterone 21-hemisuccinate; dexamethasone hemisuccinate; dexamethasone hemisuccinate: spermine; corticosterone hemisuccinate; cortexolone hemisuccinate.

Like with many other medicaments, administration of GC in a free form may posses some disadvantages, such as the risk of exposing the treated individual to side effects known to occur with GC treatment, rapid clearance of the steroid from the plasma, etc.

The present invention was aimed to provide a formulation in which GC is carried and protected in a suitable vehicle. In search for such a solution, the inventors have envisaged that while it is difficult to efficiently and stably load in a vehicle the hydrophobic GC, by applying a rather simple chemical modification on the GC involving the conversion of the steroid to a water-soluble derivate, it is possible to load the derivate into liposomes and that this resulting liposomal GC or GC derivative is effective in ameliorating symptoms of inflammation.

Thus, the present invention provides the use of a GC or a GC derivative for the preparation of a pharmaceutical composition for the treatment of an inflammatory associated condition, provided that said condition is not a neurodegenerative associated disease or disorder, wherein said GC or a GC derivative is encapsulated in a liposome and is essentially retained in said liposome for 6 months, the GC or a GC derivative being selected from:

i) an amphipathic weak base GC or GC derivative having a pKa equal or below 11 and a logD at pH 7 in the range between about −2.5 and about 1.5, preferably, in the range between about −1.5 and about 1.0;

ii) an amphipathic weak acid GC or GC derivative having a pKa above 3.5 and a logD at pH 7 in the range between about −2.5 and about 1.5, preferably, in the range between about −1.5 and about 1.0.

The term "GC derivative" as used herein denotes a GC molecule which was chemically modified either by the insertion of a chemical group or by the removal of a chemical group from the GC molecule, the modification results in the conversion of the molecule to an amphipathic weak base or amphipathic weak acid, depending on the type of modification applied. As well appreciated by those versed in the chemistry of steroids, these hydrophilic in nature molecules posses at least one chemically reactive group which may be conjugated with a weak acid or weak base to form a respective amphipathic weak acid or amphipathic weak base molecule. Non-limiting examples of chemically reactive group typically included in the general structure of steroids are hydroxyl, carboxyl, and the like, as known to those versed in chemistry. It should be noted that in the context of the present invention GC derivative may also encompass an active, non-modified, amphipathic and weakly acid GC.

The GC derivative by one aspect is a pro-drug, i.e. has not pharmaceutical activity in the form it is present in the liposome. Upon release from the liposome the GC pro-drug in converted by enzymes, such as esterases, to its pharmaceutical active hydrophobic form.

In accordance with yet another aspect the GC encapsulated in the liposome, is already in its pharmaceutically active form, and does not have to undergo any enzymatic processing in order to become active. In accordance with the second aspect the GC itself is a weak amphipathic acid or base.

The term "amphipathic weak acid" is used herein to denote a molecule having both hydrophobic and hydrophilic groups, the steroid backbone of the GC essentially constituting the hydrophobic group, while the weak acid moiety linked to the GC by virtue of the modification described above essentially constituting the hydrophilic group. The GC amphipathic weak acid or GC derivative is characterized by the following physical characteristics:

pKa: it has a pKa above 3.0, preferably above 3.5, more preferably, in the range between about 3.5 and about 6.5;

Partition coefficient: in an n-octanol/buffer (aqueous phase) system having a pH of 7.0, it has a logD in the range between about −2.5 and about 1.5 and more preferably between about −1.5 and about 1.0.

Such amphipathic weak acid derivatives of GC may be obtained by reacting the GC with dicarbocylic or tricarboxylic acids or by linking the GC to the amino group of the amino acid, by techniques known to those versed in the art.

Specific examples of GC derivates include, without being limited thereto, betamethasone 21-hemisuccinate prednisolone hemisuccinate sodium salt; prednisolone 21-hemisuccinate; dexamethasone hemisuccinate; dexamethasone hemisuccinate:spermine; corticosterone hemisuccinate prednisolone hemisuccinate; methylprednisolone hemisuccinate; dexamethasone hemisuccinate.

The term "amphipathic weak base" is used herein to denote a molecule having both hydrophobic and hydrophilic groups, the steroid backbone of the GC essentially constituting the hydrophobic group, while the weak base moiety linked to the GC by virtue of the modification described above essentially constituting the hydrophilic group. The GC amphipathic weak base derivative is characterized by the following physical characteristics:

pKa: it has a pKa below 11.0, more preferably between about 11.0 and 7.5.

Partition coefficient: in an n-octanol/buffer (aqueous phase) system having a pH of 7.0, it has a logD in the range between about −2.5 and about 1.5 and more preferably between about −1.5 and about 1.0.

Such amphipathic weak base derivatives of GC may be obtained by reacting the GC with basic amino acids, such as arginine or lysine or with any amino acid through its carboxy group, leaving the amino group free or with polyamine such as spermidine or spermine.

The term "liposome" is used herein to denote lipid based bilayer vesicles. Liposomes are widely used as biocompatible carriers of drugs, peptides, proteins, plasmic DNA, antisense oligonucleotides or ribozymes, for pharmaceutical, cosmetic, and biochemical purposes. The enormous versatility in particle size and in the physical parameters of the lipids affords an attractive potential for constructing tailor-made vehicles for a wide range of applications. Different properties (size, colloidal behavior, phase transitions, electrical charge and polymorphism) of diverse lipid formulations (liposomes, lipoplexes, cubic phases, emulsions, micelles and solid lipid nanoparticles) for distinct applications (e.g. parenteral, transdermal, pulmonary, intranasal and oral administration) are available and known to those versed in the art. These properties influence relevant properties of the liposomes, such as liposome stability during storage and in serum, the biodistribution and passive or active (specific) targeting of cargo, and how to trigger drug release and membrane disintegration and/or fusion.

The present invention is applicable for a variety of liposome compositions and those versed in the art will know how to select the constituents of the liposome depending on the various considerations including the choice of active principle (in this particular case, the specific GC or GC derivative), the mode of administration of the final liposomal composition and others.

The liposomes are those composed primarily of liposome-forming lipids which are amphiphilic molecules essentially characterized by a packing parameter 0.74-1.0, or by a lipid mixture having an additive packing parameter (the sum of the packing parameters of each component of the liposome times the mole fraction of each component) in the range between 0.74 and 1.

Liposome-forming lipids, exemplified herein by phospholipids, which form into bilayer vesicles in water. The liposomes can also include other lipids incorporated into the lipid bilayers, such as phosphatidyl ethanolamine (PE) and sterol, with their hydrophobic moiety in contact with the interior, hydrophobic region of the bilayer membrane, and the head group moiety oriented toward the exterior, polar surface of the bilayer membrane. The type and level of the additional, non-liposome forming lipid components will be determined by the additive packing parameter of the entire components of the lipid bilayer to remain in the range of 0.74-1.0.

The liposome-forming lipids are preferably those having a glycerol backbone wherein at least one, preferably two, of the hydroxyl groups at the head group is substituted with, preferably an acyl chain (to form an acyl or diacyl derivative), however, may also be substituted with an alkyl or alkenyl chain, a phosphate group or a combination or derivatives of same and may contain a chemically reactive group, (such as an amine, acid, ester, aldehyde or alcohol) at the headgroup, thereby providing a polar head group. Sphyngolipids such as sphyngomyelins, are good alternative to glycerophopholipids.

Typically, the substituting chain(s), e.g. the acyl, alkyl or alkenyl chain is between 14 to about 24 carbon atoms in length, and has varying degrees of saturation being fully, partially or non-hydrogenated lipids. Further, the lipid may be of natural source, semi-synthetic or fully synthetic lipid, and neutral, negatively or positively charged. There are a variety of synthetic vesicle-forming lipids and naturally-occurring vesicle-forming lipids, including the phospholipids, such as phosphatidylcholine (PC), phosphatidylinositol (PI), phosphatidylglycerol (PG), dimyristoyl phosphatidylglycerol (DMPG); egg yolk phosphatidylcholine (EPC), 1-palmitoyl-2-oleoylphosphatidyl choline (POPC), distearoylphosphatidylcholine (DSPC), dimyristoyl phosphatidylcholine (DMPC); phosphatidic acid (PA), phosphatidylserine (PS) 1-palmitoyl-2-oleoylphosphatidyl choline (POPC), and the sphingophospholipids such as sphingomyelins (SM) having 12-24 carbon atom acyl or alkyl chains. The above-described lipids and phospholipids whose hydrocarbon chain (acyl/alkyl/alkenyl chains) have varying degrees of saturation can be obtained commercially or prepared according to published methods. Other suitable lipids include in the liposomes are glyceroglycolipids and sphingoglycolipids and sterols (such as cholesterol or plant sterol).

Preferably, the phospholipid is egg phophatidylcholine (EPC), 1-palmitoyl-2-oleoylphosphatidyl choline (POPC), distearoylphosphatidylcholine (DSPC) or hydrogenated soy phosphatidylcholine (HSPC).

Cationic lipids (mono and polycationic) are also suitable for use in the liposomes of the invention, where the cationic lipid can be included as a minor component of the lipid composition or as a major or sole component. Such cationic lipids typically have a lipophilic moiety, such as a sterol, an acyl or diacyl chain, and where the lipid has an overall net positive charge. Preferably, the head group of the lipid carries the positive charge. Monocationic lipids may include, for example, 1,2-dimyristoyl-3-trimethylammonium propane (DMTAP) 1,2-dioleyloxy-3-(trimethylamino)propane (DOTAP); N-[1-(2,3-ditetradecyloxy)propyl]-N,N-dimethyl-N-hydroxyethylammonium bromide (DMRIE); N-[1-(2,3,-dioleyloxy)propyl]-N,N-dimethyl-N-hydroxy ethyl-ammonium bromide (DORIE); N-[1-(2,3-dioleyloxy) propyl]-N,N,N-trimethylammonium chloride (DOTMA); 3β[N-(N',N'-methylaminoethane)carbamoly]cholesterol (DC-Chol); and dimethyl-ioctadecylammonium (DDAB).

Examples of polycationic lipids include a similar lipophilic moiety as with the mono cationic lipids, to which polycationic moiety is attached. Exemplary polycationic moieties include spermine or spermidine (as exemplified by DOSPA and DOSPER), or a peptide, such as polylysine or other polyamine lipids. For example, the neutral lipid (DOPE) can be derivatized with polylysine to form a cationic lipid. polycationic lipids include, without being limited thereto, N-[2-[[2,5-bis[3-aminopropyl)amino]-1-oxopentyl]amino]ethyl]-N,N-dimethyl-2,3-bis[(1-oxo-9-octadecenyl)oxy]-1-propanaminium (DOSPA), and ceramide carbamoyl spermine (CCS).

The lipids mixture forming the liposome can be selected to achieve a specified degree of fluidity or rigidity, to control the stability of the liposome in serum and to control the rate of release of the entrapped agent in the liposome.

Further, the liposomes may also include a lipid derivatized with a hydrophilic polymer to form new entities known by the term lipopolymers. Lipopolymers preferably comprise lipids modified at their head group with a polymer having a molecular weight equal or above 750 Da. The head group may be polar or apolar, however, is preferably a polar head group to which a large (>750 Da) highly hydrated (at least 60 molecules of water per head group) flexible polymer is attached. The attachment of the hydrophilic polymer head group to the lipid region may be a covalent or non-covalent attachment, however, is preferably via the formation of a covalent bond (optionally via a linker). The outermost surface coating of hydrophilic polymer chains is effective to provide a liposome with a long blood circulation lifetime in vivo. The lipopolymer may be introduced into the liposome by two different ways: (a) either by adding the lipopolymer to a lipid mixture forming the liposome. The lipopolymer will be incorporated and exposed at the inner and outer leaflets of the liposome bilayer [Uster P. S. et al. FEBBS Letters 386:243 (1996)]; (b) or by firstly prepare the liposome and then incorporate the lipopolymers to the external leaflet of the pre-formed liposome either by incubation at temperature above the Tm of the lipopolymer and liposome-forming lipids, or by short term exposure to microwave irradiation.

Preparation of vesicles composed of liposome-forming lipids and derivatization of such lipids with hydrophilic polymers (thereby forming lipopolymers) has been described, for example by Tirosh et al. [Tirosh et al., Biopys. J., 74(3):1371-1379, (1998)] and in U.S. Pat. Nos. 5,013,556; 5,395,619; 5,817,856; 6,043,094, 6,165,501, incorporated herein by reference and in WO 98/07409. The lipopolymers may be non-ionic lipopolymers (also referred to at times as neutral lipopolymers or uncharged lipopolymers) or lipopolymers having a net negative or a net positive charge.

There are numerous polymers which may be attached to lipids. Polymers typically used as lipid modifiers include, without being limited thereto: polyethylene glycol (PEG), polysialic acid, polylactic (also termed polylactide), polyglycolic acid (also termed polyglycolide), apolylactic-polyglycolic acid, polyvinyl alcohol, polyvinylpyrrolidone, polymethoxazoline, polyethyloxazoline, polyhydroxyethyloxazoline, polyhydroxypropyloxazoline, polyaspartamide, polyhydroxypropyl methacrylamide, polymethacrylamide, polydimethylacrylamide, polyvinylmethylether, polyhydroxyethyl acrylate, derivatized celluloses such as hydroxymethylcellulose or hydroxyethylcellulose. The polymers may be employed as homopolymers or as block or random copolymers.

While the lipids derivatized into lipopolymers may be neutral, negatively charged, as well as positively charged, i.e. there is no restriction to a specific (or no) charge, the most commonly used and commercially available lipids derivatized into lipopolymers are those based on phosphatidyl ethanolamine (PE), usually, distearylphosphatidylethanolamine (DSPE).

A specific family of lipopolymers employed by the invention include monomethylated PEG attached to DSPE (with different lengths of PEG chains, the methylated PEG referred to herein by the abbreviation PEG) in which the PEG polymer is linked to the lipid via a carbamate linkage resulting in a negatively charged lipopolymer. Other lipopolymers are the neutral methyl polyethyleneglycol distearoylglycerol (mPEG-DSG) and the neutral methyl polyethyleneglycol oxycarbonyl-3-amino-1,2-propanediol distearoylester (mPEG-DS) [Garbuzenko O. et al., Langmuir. 21:2560-2568 (2005)]. The PEG moiety preferably has a molecular weight of the head group is from about 750 Da to about 20,000 Da. More preferably, the molecular weight is from about 750 Da to about 12,000 Da and most preferably between about 1,000 Da to about 5,000 Da. One specific PEG-DSPE employed herein is that wherein PEG has a molecular weight of 2000 Da, designated herein $^{2000}$PEG-DSPE or $^{2k}$PEG-DSPE.

Preparation of liposomes including such derivatized lipids has also been described, where typically, between 1-20 mole percent of such a derivatized lipid is included in the liposome formulation.

It is well established that preparation of liposomal formulation involve the selection of an appropriate lipid composition in addition to the aqueous phase ingredients, such as buffers, antioxidants, metal chelators, and cryoprotectants. Charge-inducing lipids, such as phosphatidylglycerol can be incorporated into the liposome bilayer to decrease vesicle-vesicle fusion and to increase interaction with cells, while cholesterol and sphingomyelin can be included in formulations in order to decrease permeability and leakage of encapsulated drugs. Buffers at neutral pH can decrease hydrolysis. Addition of an antioxidant, such as sodium ascorbate can decrease oxidation. Etc.

Variations in ratios between these liposome constituents dictate the pharmacological properties of the liposome, including stability of the liposomes, which is a major concern for various types of vesicular applications. Evidently, the stability of liposomes should meet the same standards as conventional pharmaceuticals. Chemical stability involves prevention of both the hydrolysis of ester bonds in the phospholipid bilayer and the oxidation of unsaturated sites in the lipid chain. Chemical instability can lead to physical instability or leakage of encapsulated drug from the bilayer and fusion and aggregation of vesicles. Chemical instability also results in short blood circulation time of the liposome, which affects the effective access to and interaction with the target.

A preferred formulation according to the invention is that comprising phosphatidylcholine (PC) such as egg PC (EPC) or hydrogenated soy PC (HSPC) as a the liposome forming lipid, PEGylated (2000 Da) distearoyl-phosphatidylethanolamine (PEG-DSPE) and cholesterol. Evidently, other lipids mixtures may be utilized in the same, similar or different mole ratio, and provided that the final additive packing parameter of the different constituents of the liposome is in the range of between about 0.74 and 1.0.

Figure 3A:
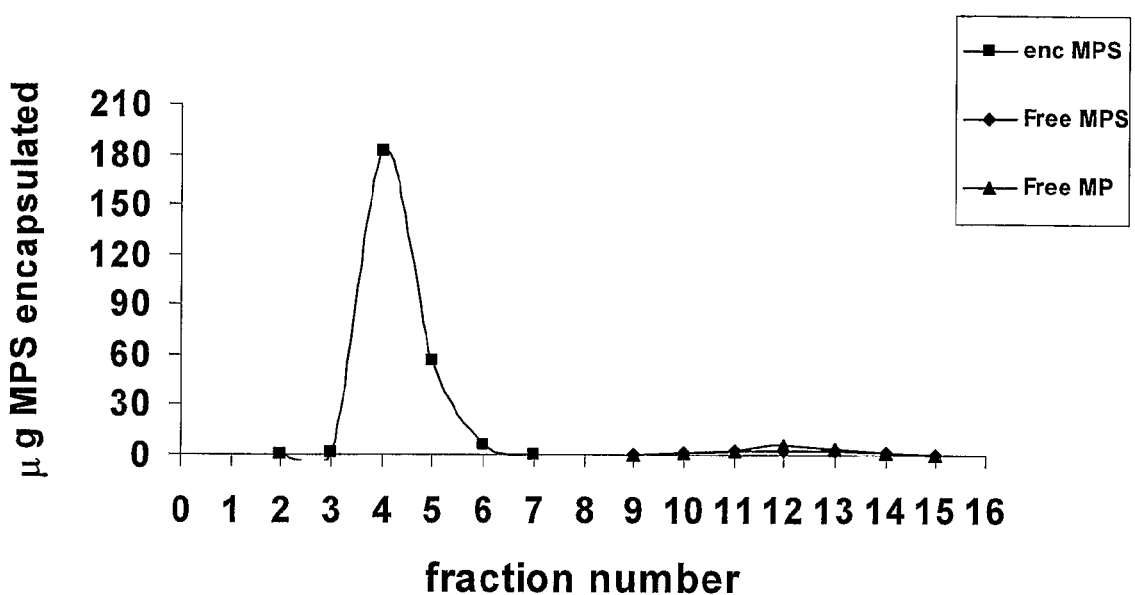
FIG. 3A-3B are size exclusion chromatography of SSL-MPS after 14 months of storage at 4° C., showing encapsulated MPS (enc-MPS), free MPS (free-MPS) an free methylprednisolone (free-MP), with FIG. 3B being an enlargement of the section describing fractions 8-17 of FIG. 3A showing existence of very low amounts of free MPS and (MP).
Figure 3B:
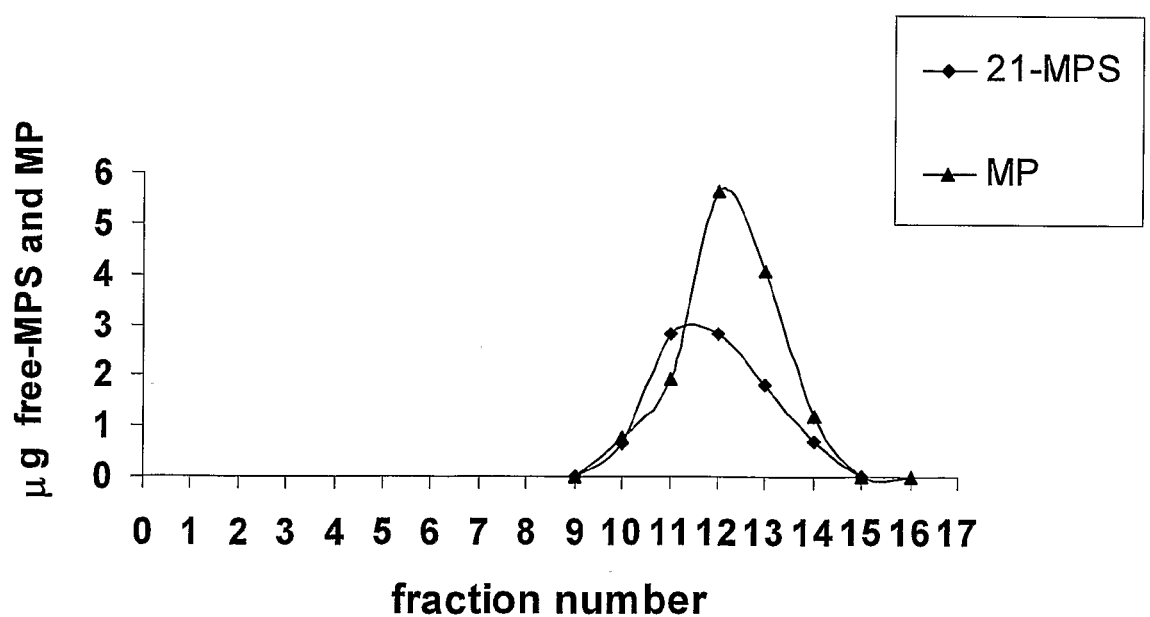

The pharmaceutical formulation of the invention was proven to be highly stable. An exemplified embodiment of the invention in which the GC derivative, Methylprednisolone hemisuccinate (methylprednisolone modified with succinic acid) was encapsulated in a liposome comprising the above three constituents, was shown to have only marginal reduction (less than 20% from initial concentration) in the GC derivative after storage at 4° C. for 14 months (FIGS. 3A-3B).

Thus, in the context of the present invention, the term "stability" denotes a formulation which under conventional storage conditions (4° C.) retains the majority (more than 80%, preferably more than 90%) of the GC/GC derivative in the liposome, for 6 months, preferably for 10 months and more preferably for 14 months. Accordingly, the term "essentially retains" used herein denotes that 80% and preferably 90% of the GC/GC derivative is retained in the liposomes under storage conditions for about 6, preferably 10 and more preferably 14 months. According to one preferred embodiment, stability of the liposomes is maintained by the use of sterically stabilized liposome (SSL), i.e. liposomes coated with a hydrophilic component. According to a preferred embodiment, the SSL comprises a combination of hydrogenated soy phosphatidylcholine (HSPC), $^{2000}$PEG-DSPE and cholesterol at a mole ratio of 55:40:5.

In general, there are a variety of drug-loading methods available for preparing liposomes with entrapped drug, including passive entrapment and active remote loading. The passive entrapment method is most suited for entrapping of lipophilic drugs in the liposome membrane and for entrapping drugs having high water solubility. In the case of ionizable hydrophilic or amphipathic drugs, even greater drug-loading efficiency can be achieved by loading the drug into liposomes against a transmembrane ion gradient [Nichols, J. W., et al., Biochim. Biophys. Acta 455:269-271 (1976); Cramer, J., et al., Biochemical and Biophysical Research Communications 75(2):295-301 (1977)]. This loading method, generally referred to as remote loading, typically involves a drug which is amphipathic in nature and has an ionizable group which is loaded by adding it to a suspension of liposomes having a higher inside/lower outside $H^+$ and/or ion gradient.

The liposomes employed in the context of the present invention are preferably loaded by the remote loading principle. The resulting formulation exhibited a significantly high GC/GC derivative to lipid ratio. Preferably, the mole ratio between the GC/GC derivative and lipid is between 0.01 and 2.0, more preferably, between 0.04 and 0.25. For high loading of the amphipathic weak base/base it is at times preferable that the concentration of the same in the liposome be such that it precipitates in the presence of a pre-entrapped counter ion.

Liposomes having an $H^+$ and/or ion gradient across the liposome bilayer for use in remote loading can be prepared by a variety of techniques. A typical procedure comprises dissolving a mixture of lipids at a ratio that forms stable liposomes in a suitable organic solvent and evaporated in a vessel to form a thin lipid film. The film is then covered with an aqueous medium containing the solute species that will form the aqueous phase in the liposome interior space. After liposome formation, the vesicles may be sized to achieve a size distribution of liposomes within a selected range, according to known methods. The liposomes utilized in the present invention are preferably uniformly sized to a selected size range between 70-100 nm, preferably about 80 nm.

After sizing, the external medium of the liposomes is treated to produce an ion gradient across the liposome membrane (typically with the same buffer used to form the liposomes), which is typically a higher inside/lower outside ion concentration gradient. This may be done in a variety of ways, e.g., by (i) diluting the external medium, (ii) dialysis against the desired final medium, (iii) gel exclusion chromatography, e.g., using Sephadex G-50, equilibrated in the desired medium which is used for elution, or (iv) repeated high-speed centrifugation and resuspension of pelleted liposomes in the desired final medium. The selection of the external medium will depend on the type of gradient, on the mechanism of gradient formation, the external solute and pH desired, as will now be described.

In the simplest approach for generating an ion and/or $H^+$ gradient, the lipids are hydrated and sized in a medium having a selected internal-medium pH. The suspension of the liposomes is titrated until the external liposome mixture reaches the desired final pH, or treated as above to exchange the external phase buffer with one having the desired external pH. For example, the original hydration medium may have a pH of 5.5, in a selected buffer, e.g., glutamate, citrate, succinate, fumarate buffer, and the final external medium may have a pH of 8.5 in the same or different buffer. The common characteristic of these buffers is that they are formed from acids which are essentially liposome impermeable. The internal and external media are preferably selected to contain about the same osmolarity, e.g., by suitable adjustment of the concentration of buffer, salt, or low molecular weight non-electrolyte solute, such as dextrose or sucrose.

In another general approach, the gradient is produced by including in the liposomes, a selected ionophore. To illustrate, liposomes prepared to contain valinomycin in the liposome bilayer are prepared in a potassium buffer, sized, then the external medium exchanged with a sodium buffer, creating a potassium inside/sodium outside gradient. Movement of potassium ions in an inside-to-outside direction in turn generates a lower inside/higher outside pH gradient, presumably due to movement of protons into the liposomes in response to the net electronegative charge across the liposome membranes [Deamer, D. W., et al., Biochim. et Biophys. Acta 274:323 (1972)].

A similar approach is to hydrate the lipid and to size the formed multilamellar liposome in high concentration of magnesium sulfate. The magnesium sulfate gradient is created by dialysis against 20 mM HEPPES buffer, pH 7.4 in sucrose. Then, the A23187 ionophore is added, resulting in outwards transport of the magnesium ion in exchange for two protons for each magnesium ion, plus establishing a inner liposome high/outer liposome low proton gradient [Senske D B et al. (Biochim. Biophys. Acta 1414: 188-204 (1998)].

In another more preferred approach, the proton gradient used for drug loading is produced by creating an ammonium ion gradient across the liposome membrane, as described, for example, in U.S. Pat. Nos. 5,192,549 and 5,316,771, incorporated herein by reference. The liposomes are prepared in an aqueous buffer containing an ammonium salt, such as ammonium sulfate, ammonium phosphate, ammonium citrate, etc., typically 0.1 to 0.3 M ammonium salt, at a suitable pH, e.g., 5.5 to 7.5. The gradient can also be produced by including in the hydration medium sulfated polymers, such as dextran sulfate ammonium salt, heparin sulfate ammonium salt or sucralfate. After liposome formation and sizing, the external medium is exchanged for one lacking ammonium ions. In this approach, during the loading the amphipathic weak base is exchanged with the ammonium ion.

Yet, another approach is described in U.S. Pat. No. 5,939,096, incorporated herein by reference. In brief, the method employs a proton shuttle mechanism involving the salt of a weak acid, such as acetic acid, of which the protonated form trans-locates across the liposome membrane to generate a higher inside/lower outside pH gradient. An amphipathic weak acid compound is then added to the medium to the pre-formed liposomes. This amphipathic weak acid accumulates in liposomes in response to this gradient, and may be retained in the liposomes by cation (i.e. calcium ions)-promoted precipitation or low permeability across the liposome membrane, namely, the amphipathic weak acid is exchanges with the acetic acid.

The thus formed liposomes loaded with the GC or GC derivative may be then be used for treatment of subjects having or in disposition of developing a medical condition associated with the immune system.

The terms "inflammatory associated condition" which may be used interchangeably with the term "inflammatory state" refers to any disease or pathological conditions wherein one of the manifestation is the present of inflammation. The inflammation may be the underlying cause of the disease or pathological condition, or may be the results or another physiological process underlying the condition. This term refers to any state of active or sub-clinical inflammation, including immune induced pathologies (e.g. autoimmune disorders). The inflammation may be due to an inflammatory disease, or it may be a side effect of some other type of disease or disorder.

Inflammatory states and other immune induced pathologies which are mediated by the immune system may be divided into four categories:

I. Immediate hypersensitivity (allergic, or reaginic acute inflammation): includes type I hypersensitivity and is characterized by an allergic reaction that occurs immediately following contact with antigen (allergen). In some individuals certain allergens have a propensity to stimulate production of IgE antibodies. IgE antibodies bind nonspecifically, via their high affinity Fc receptors, to mast cells and basophils. Subsequent attachment of antigen to the Fab portion of cell-bound IgE antibodies results in release of contents of cytoplasmic granules from mast cells and basophils (e.g. histamine), as well as in synthesis and secretion of biologically active products of arachidonic acid (e.g. leukotrienes).

Allergic reactions include, without being limited thereto urticaria, seasonal rhinitis, asthma, and in settings where large amounts of antigens (allergens) enter the host circulation, systemic anaphylaxis.

Another non-limiting example of a type I hypersensitivity is septic shock.

II. Cytotoxic (inflammation mediated by cytotoxic antibodies): refers to Type II, or antibody-dependent cytotoxic hypersensitivity and occurs when antibody binds to either self antigen or foreign antigen on cells, and leads to phagocytosis, killer cell activity or complement-mediated lysis.

In type II hypersensitivity, also known by the term antibody directed against cell surface or tissue antigens forms immune complex which interacts with complement and a variety of effector cells to bring about damage to the target cells. Antibodies link the target cells to effectors cells, such as macrophages, neutrophils, eosinophils and generally, K cells, by means of Fc receptors on these effector cells.

Both the complement fragments and IgG can act as opsonins bound to host tissues or to microorganisms, and phagocytes take up the opsonized particles.

There are three main subtypes of cytotoxic hypersensitivity:

(a) Type II reactions between members of the same species caused by isoimmunization and include transfusion reactions after transfusion of blood incompatible in the ABO system, haemolytic disease of the newborn due to rhesus incompatibility and/or transplantation reaction provoked by antibodies in the recipient directed against surface transplantation antigens on the graft.

(b) Autoimmune type II hypersensitivity reactions evoked by antibodies in the host directed against his own cell or tissue antigens (autoantibodies). As an example may serve autoimmune haemolytic anaemia caused by autoantibodies to the patient's own red cells; Hashimoto's thyroiditis with autoantibodies against thyroid peroxidase surface antigen; idiopathic thrombocytopenic purpura manifest by platelet destruction evoked by anti-platelet antibodies; Goodpasture's syndrome in which complement-mediated damage to basement membrane due to specific autoantibodies is observed.

The following is a non-limiting list of autoimmune diseases which may be treated in accordance with the present invention: Tropical spastic paraparesis, , Acute necrotizing hemorrhagic leukoencephalitis, Paraneoplastic, Hashimoto's thyroiditis, Postpartum thyroiditis, Focal thyroiditis, Juvenile thyroiditis, Idiopathic hypothyroidism, Type I (insulin dependent) diabetes mellitus, Addison's disease, Hypophysitis, Autoimmune diabetes insipidus, Hypoparathyroidism, Pemphigus Vulgaris, Pemphigus Foliaceus, Bullous pemphigoid/Pemphigoid gestationis, Cicatrical pemphigoid, Dermatitis herpetiformis, Epidermal bullosa acquisita, Erythema multiforme, Herpes gestatonis, Vitiligo, Chronic urticaria, Discoid lupus, Alopecia universalis/Areata, Psoriasis, Autoimmune hepatitis, Primary biliary cirrhosis, Chronic active hepatitis, Chronic active hepatitis/Primary biliary cirrhosis overlap syndrome, Primary sclerosing cholangitis, Autoimmune hemolytic anemia, Idiopathic thrombocytopenic purpura, Evans syndrome, Heparin-induced thrombocytopenia, Primary autoimmune neutropenia, Autoimmune (primary) neutropenia of infancy, Autoimmune neutropenia following bone marrow transplant, Acquired autoimmune hemophilia, Autoimmune gastritis and pernicious anemia, Coeliac disease, Crohn's disease, Ulcerative colitis, inflammatory bowel diseases (IBD), Sialadenitis, Autoimmune premature ovarian failure, Azoospermia, Hypogonadism, Male infertility associated with sperm autoantibodies, Autoimmune orchitis, Premature ovarian failure, Autoimmune oophoritis, Uveitis, Retinitis, Sympathetic ophthalmia, Birdshot retinochoroidopathy, Vogt-Koyanagi-Harada granulomatous uveitis, Lens-induced uveitis, Autoimmune myocarditis, Congenital heart block (neonatal lupus), Chagas' disease, Adriamycin cardiotoxicity, Dressler's myocarditis syndrome, Bronchial asthma, Interstitial fibrosing lung disease, Rapidly progressive glomerulonephritis, Autoimmune tubulointerstitial nephritis, Systemic lupus erythematosus (SLE), Antiphospholipid syndrome, Rheumatoid arthritis, Juvenile Rheumatoid arthritis, Felty's syndrome, Large granular lymphocytosis (LGL), Sjogren's syndrome, Systemic sclerosis (scleroderma), Crest syndrome, Mixed connective tissue disease, Polymyositis/dermatomyositis, Goodpasture's Disease, Wegener's granulomatosis, Churg-Strauss syndrome, Henoch-Schonlein purpura, Microscopic polyangiatis, Periarteritis nodosa, Bechet's syndrome, Atherosclerosis, Temporal (giant) cell arteritis, Takayasu arteritis, Kawasaki disease, Ankylosing spondilitis, Reiter's disease, Sneddons disease, Autoimmune polyendocrinopathy, candidiasis-ectodermal dystropy, Essential cryoglobulinemic vasculitis, Cutaneous leukocytoclastic angiitis, Lyme disease, Rheumatic fever and heart disease, Eosinophilic fasciitis, Paroxysmal cold hemoglobinuria, Polymyalgia rheumatica, Fibromyalgia, POEMS syndrome (polyneuropathy, organomegaly, endocrinopathy, M-spot and skin changes), Relapsing polychondritis, Autoimmune lymphoproliferative syndrome, TINU syndrome (acute tubulointerstitial nephritis and uveitis), Common variable immunodeficiency, TAP (transporter associated with antigen presentation) deficiency, Omenn syndrome, HyperIgM syndrome, BTK agammaglobulinemia, Human immunodeficiency virus and Post bone-marrow-transplant.

(c) Type II drug reactions in which drugs may become coupled to body components and thereby undergo conversion from a hapten to a full antigen which may sensitive certain individuals. If, during this response, IgE antibodies are produced, anaphylactic reactions can result. In some circumstances, cell-mediated hypersensitivity may by induced. In other cases where coupling to serum proteins occurs, the possibility of type III immune complex-mediated reactions may arise. Finally, the drug antigenic complex with a molecule on the surface of host cells may evoke the production of antibodies which are cytotoxic for the cell-drug complex. Examples of this mechanism have been seen in the haemolytic anaemia sometimes associated with continued administration of chlorpromazine or phenacetin, in the agranulocytosis associated with the taking of amidopyrine or of quinidine, and classic situation of thrombocytopenic purpura which may be produced by a sedative edormid. When the drug is withdrawn, the hypersensitivy is no longer evident.

III. Immune complex (inflammation mediated by immune complex) which may be broadly divided into three groups:

(a) A combined effect of a low-grade persistent infection together with a weak antibody response, leading to chronic immune complex formation with the eventual deposition of complexes in the tissues.

(b) Immune complex disease as a complication of autoimmune disease where the continued produced of antibody to a self-antigen leads to prolonged immune complex formation. The mononuclear phagocyte, erythrocyte, and complement systems (which are responsible for the removal of complexes) become overloaded and the complexes are deposited in the tissues, as occurs in systemic lupus erythematosus.

(c) Immune complexes formed at body surfaces, notably in the lungs following repeated inhalation of antigenic material from moulds, plants or animals. This is exemplified in Farmer's lung and Pigeon fancier's lung, where there are circulating antibodies to the actinomycete fungi found in mouldy hay, or to pigeon antigens. Both diseases are forms of extrinsic allergic alveolitis, and they only occur after repeated exposure to the antigen.

IV. Delayed hypersensitivity (chronic inflammation mediated by lymphocytes and macrophages, DTH)—manifested when antigens (for example those of tubercle bacilli) are trapped in a macrophage and cannot be cleared. T cells are then stimulated to elaborate lymphokines which mediate a range of inflammatory responses. Other aspects of DTH reactions are seen in graft rejection and allergic contact dermatitis. DTH is used as a general category to describe all those hypersensitivity reactions which take more than 12 hours to develop, and which involve cell-mediated immune reactions rather than humoral immune reactions. Whereas allergic reactions occur within seconds and minutes and immune complex reactions occur within several hours to one day, DTH reactions peak at 2 to 3 days.

Three types of delayed hypersensitivity reaction are recognized: Contact hypersensitivity and tuberculin-type hypersensitivity both occur within 72 hours of antigen challenge, whereas granulomatous reactions develop over a period of weeks. The granulomas are formed by the aggregation and proliferation of macrophages, and may persist for weeks.

According to a preferred embodiment, the inflammatory associated condition is associated with an autoimmune response selected from rheumatoid arthritis, Crohn's disease & colitis (collectively referred to as IBD—Inflammatory Bowel disease) and diabetes mellitus The present invention specifically excludes any condition which may also be regarded as associated with a neurodegenerative disease or disorder. The term "associated neurodegenerative disease or disorder", or in short, "neurodegenerative condition", in the context of the present invention denotes any abnormal deterioration of the nervous system resulting in the dysfunction of the system. Further, it denotes a group of conditions in which there is gradual, generally relentlessly progressive wasting away of structural elements of the nervous system exhibited by any parameter related decrease in neuronal function, e.g. a reduction in mobility, a reduction in vocalization, decrease in cognitive function (notably learning and memory) abnormal limb-clasping reflex, retinal atrophy inability to succeed in a hang test, an increased level of MMP-2, an increased level of neurofibrillary tangles, increased tau phosphorylation, tau filament formation, abnormal neuronal morphology, lysosomal abnormalities, neuronal degeneration, gliosis and demyelination.

Without being limited thereto, neurodegenerative conditions may be classified according to the following groups:

Demyelinating and neuroautoimmune diseases, including, without being limited thereto acute, chronic progressive, and relapsing remitting multiple sclerosis (MS), Devic's disease, optic neuritis, acute disseminated encephalomyelitis, Guillain-Barre syndrome, chronic inflammatory demyelinating polyradiculoneuropathy, vasculitis, neural effect of systemic lupus erythematosus, neurosarcoidosis.

Infectious diseases, including, without being limited thereto cerebral malaria, post viral infectious encephalitis and Bell palsy.

Neurodegenerative disorders, including, without being limited thereto Alzheimer's disease, Parkinson's disease, senile dementias, prion diseases, spongiform encephalopathy, Creutzfeldt-Jakob disease, AIDS dementia, tauopathies and amyotrophic lateral sclerosis.

Brain Trauma, including, without being limited thereto, stroke, closed head injury, radiation injury and spinal cord trauma.

Considering the above, the invention also provides a method for the treatment of an inflammatory associated condition I (excluding conditions which may also be classified as a neurodegenerative condition, such as multiple sclerosis), the method comprises administering to said subject an effective amount of the liposomal GC or GC derivative.

Yet, the invention provides a pharmaceutical composition comprising the liposomal GC or GC derivative as defined, for the above defined treatment. The liposomal GC/GC derivative may be formulated in combination with physiologically acceptable excipients, as known in the art. The pharmaceutically acceptable excipient employed according to the invention generally refers to inert, non-toxic substances which preferably do not react with liposomes. The excipient may be any of those conventionally used and is limited only by chemical-physical considerations, such as solubility and lack of reactivity with liposomes, and by the route of administration. The carrier may also at times have the effect of the improving the delivery or penetration of the liposomal formulation to a target tissue, for improving the stability of the liposomal formulation, for slowing clearance rates, for imparting slow release properties, for reducing undesired side effects etc. The excipient may also be a substance that stabilizes the formulation (e. g. a preservative), for providing the formulation with an edible flavor, etc. The carrier may include additives, colorants, diluents, buffering agents, disintegrating agents, moistening agents, preservatives, flavoring agents etc.

The pharmaceutical composition may also comprise other active principles as known to those versed in disorders of the immune system, such as immunosuppressive agents.

The terms "treat", "treating" and "treatment" refer to the administering of a therapeutically effective anti-inflammatory amount of the liposome encapsulated GC/GC derivative or a pharmaceutical composition comprising same which is effective to ameliorate undesired symptoms associated with a disease or disorder of the immune system (inflammation and immune induced pathologies), to prevent the manifestation of such symptoms before they occur, to slow down the progression of the medical condition, to slow down the deterioration of symptoms associated with the condition, to slow down the irreversible damage caused by the chronic stage of the condition, to lessen the severity or cure an the condition, to improve survival rate or more rapid recovery form such a condition.

It should be noted that in the context of the present invention the term "treatment" also denotes "prophylactic treatment", i.e. for prevention of the development of the inflammatory associated condition, or to prevent the re-occurrence of an acute phase of the condition in a chronically ill individual. To this end, liposomes encapsulating the GC/GC derivative may be administered to individuals who do not have inflammation or an autoimmune disorder and especially, to individuals having a high-risk of developing a medical condition associated with the immune system, e.g. as a result of injury, exposure to an infecting agent or allergen, in order to delay the onset of the disease. In this case, the liposome encapsulated GC/GC derivative will typically be administered over an extended period of time in a single daily dose (e.g. to produce a cumulative effective amount), in several doses a day, as a single dose for several days, etc. so as to prevent the manifestation of inflammation or an autoimmune reaction.

The "anti-inflammatory effective amount" for purposes herein is determined by such considerations as may be known in the art. The amount must be effective to achieve the desired anti-inflammatory effect in a subject suffering from an inflammatory or autoimmune state as indicated above.

The effective amount depends, inter alia, on the type and severity of the disease to be treated and the treatment regime. The effective amount is typically determined in appropriately designed clinical trials (dose range studies) and the person versed in the art will know how to properly conduct such trials in order to determine the effective amount. As generally known, an effective amount depends on a variety of factors including the affinity of the molecule to the corresponding receptor, its distribution profile within the body, a variety of pharmacological parameters such as half life in the body, on undesired side effects, if any, on factors such as age and gender, etc.

As used herein, "administering" is used to denote the contacting or dispensing, delivering or applying the liposomal formulation, to a subject by any suitable route for delivery thereof to the desired location in the body, these include oral, parenteral (including subcutaneous, intramuscular and intravenous, intraarterial, intraperitoneally) and intranasal administration as well as by as well as intrathecal and infusion techniques.

According to one embodiment, the liposomal formulations used in accordance with the invention are in a form suitable for injection. The requirements for effective pharmaceutical vehicles for injectable formulations are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4$^{th}$ ed., pages 622-630 (1986).The effective amount may be that provided in a single dose or a cumulative amount provided to a subject in several doses provided to a subject over an extended period of time (e.g. in a single daily dose) or in several doses a day.

It is noted that humans are treated generally longer than experimental animals as exemplified herein, which treatment has a length proportional to the length of the disease process and active agent effectiveness. The doses may be a single dose or multiple doses given over a period of several days.

While the following disclosure provides experimental data with animal model, there are a variety of acceptable approaches for converting doses from animal models to humans. For example, calculation of approximate body surface area (BSA) approach makes use of a simple allometric relationship based on body weight (BW) such that BSA is equal to body weight (BW) to the 0.67 power [Freireich E. J. et al. Cancer Chemother. Reports 1966, 50(4) 219-244; and as analyzed in Dosage Regimen Design for Pharmaceutical Studies Conducted in Animals, by Mordenti, J, in J. Pharm. Sci., 75:852-57, 1986]. Further, allometry and tables of BSA data have been established [Extrapolation of Toxicological and Pharmacological Data from Animals to Humans, by Chappell W & Mordenti J, Advances in Drug Research, Vol. 20, 1-116, 1991 (published by Academic Press Ltd)]

Another approach for converting doses is a pharmacokinetic-based approach using the area under the concentration time curve (AUC) or Physiologically Based PharmacoKinetic (PBPK) methods are described [Voisin E. M. et al. Regul Toxicol Pharmacol. 12(2): 107-116. (1990)]

DESCRIPTION OF SPECIFIC EXAMPLES

General

Materials

Hydrogenated soybean phosphatidylcholine (HSPC) was obtained from Lipoid KG (Ludwigshafen, Germany).

N-carbamyl-poly-(ethylene glycol methyl ether)-1,2-distearoyl-sn-glycero-3-phosphoethanolamine triethyl ammonium salt (PEG-DSPE) (the polyethylene moiety of this phospholipid having a molecular mass of 2000 Da) was obtained from Genzyme Liestale, Switzerland.

Cholesterol (>99% pure) was obtained from Sigma (St. Louis, Mo., USA).

[$^3$H] Cholesteryl hexadecyl ether (45 Ci per mmol) was from NEN Life Science Products (Boston, Mass., USA). tert-Butanol (99% pure) was purchased from BDH, Poole, UK.

The weak acid steroids, the pro-drugs methylprednisolone sodium hemisuccinate (MPS) and hydrocortisone sodium hemisuccinate (HYD), were obtained from Pfeizer, Belgium All the other chemicals, including buffers were of analytical grade or better, and were obtained from Sigma. Purified water was obtained from WaterPro PS IPLC/Ultrafilter Hybrid model, (Labconco, Kansas City, Mo., USA).

Methods

Liposome Preparation

A stock solution HSPC/Cholesterol/PEG-DSPE-2000 at mole ratio of 55:40:5 was dissolved in ethanol at 70° C. to a final gel lipid concentration of 62.5% (w/v). The solution was then incubated at 70° C. until all the lipids are dissolved to a clear solution. The stock solution was then added to a solution of calcium acetate 200 mM at 70° C. to receive 10% lipid concentration (w/v) hence reaching a final ethanol concentration of 16% (w/v). The mixture was constantly stirred at 70° C. to receive a milky dispersion at this stage lipids were hydrated to form multi lamellar liposome (MLV) dispersion.

The vesicles that were formed were downsized using extrusion through a polycarbonate filter of defined pore size starting with 400-nm and ending with 50-nm pore size filters, as the last extrusion step under low to medium pressure. This processes results in 80±15-nm liposomes. The extrusion device (Northern Lipids, Canada) was kept in a constant temperature of 70° C. during the entire procedure.

The removal of extraliposomal Ca acetate to create the Ca acetate gradient {[Ca acetate] in liposome>>[Ca acetate] in medium} was created by dialysis against dextrose 5% or saline 0.9 at 4° C. (4 exchanges×100 volume each, the final one over night).

Liposome phospholipids concentration was determined from organic phosphorus concentration by a modified Bartlet procedure [Shmeeda, H., et al. In: Methods in Enzymology "Liposomes", (Düzgünes, N., ed.), 367:272-292 (2003)]. Lipid concentration in the resulting liposome stock solution was ~40 mM.

The amount of calcium inside the liposomes was determined by the use of atomic absorption spectrometry (AAS).

Preparation and Characterization of Radioactive-SSL

[$^3$H] cholesteryl ether-labeled sterically stabilized liposomes (SSL) composed of HSPC:Chol:$^{2000}$PEG-DSPE (55:40:5 mole ratio), and a trace amount of [$^3$H] cholesteryl hexadecyl ether (0.125 µCi/µmol PL) were prepared as described above. The liposome size was determined by Dynamic Light Scattering (DLS) to be 87±15 nm.

Loading of MPS Into Liposomes

A stock solution of methylprednisolone hemisuccinate sodium salt (MPS, the GC derivative) was dissolved in 5% dextrose (pH 7.2) to a concentration of ~9 mg/ml and added to the preformed SSL dispersion after the calcium acetate gradient was established. MPS concentration was ~9 mg/ml and phospholipid ~32 mM phosphate.

Loading was achieved by incubation of the components above for the desired time at 62° C. (above matrix lipid $T_m$). Liposomes were then cooled to 4° C. and dialyzed against 5% dextrose at 4° C. to remove acetate released during loading and to remove unloaded drug or alternatively unloaded drug was removed by the ion exchanger Dowex 1×400 mesh (Cl$^-$ form).

State of Aggregation, Partition Coefficient and Surface Tension of MPS

1. State of Aggregation of MPS

Aggregation of MPS was determined from the change in turbidity measured as intensity of light scattered at 90° to excitation beam using a spectrofluormeter under conditions that MPS lack absorbance (excitation and emission at the same wavelength Ex=600 nm Em=600 nm). There is a large increase in the light scattered by MPS solution/dispersion due to formation of aggregates.

The intensity of scattered light (at 90° to the excitation), also defined as turbidity is proportional to concentration and to the size of the aggregates. [Zuidam, N. J. and Barenholz, Y., *Biochim. Biophys. Acta* 1368:115-128 (1998)]. The state of aggregation of MPS was tested in the following manner: To quartz cuvette MPS (2 ml) at concentration of ~6.5mg/ml MPS was added. The solution was tittered with HCl (1.756 M) and light scattering using excitation and emission at (both at 600 nm with attenuation of 1%) and pH of the solution was monitored.

2. Partition Coefficient

Partition coefficient (logD) of some GC derivatives (which are amphipathic weak acids) was determined by the 'shake flask' as described [Samuni, A. M. and Barenholz, Y., *Free Radicals Biol. Med.* 22:1165-1174 (1997)].

3. Surface Tension

Surface tension was measured using µtrouge S (Kibron Inc., Helsinki Finland). A solution containing GC derivative (300 µL) was placed in the well after calibration and zeroing of the sensor using pure water and air. The measurement was performed at 26° C.

Precipitation of MPS Inside SSL

MPS precipitation inside the intraliposomal aqueous phase of the vesicle was visualized using Cryo TEM as described [Lasic, D. D., Frederik, P. M., Stuart, M. C. A., Barenholz, Y. and McIntosh, T. J., Gelation of liposome interior. A novel method for drug encapsulation. *FEBS Lett.* 312, 255-258 (1992); Lasic, D. D., et al. *Biochim. Biophys. Acta* 1239, 145-156 (1995)].

Precipitation Studies

To 600 mOsm Ca-acetate solution at 63° C and at different pH points MPS was added at final concentration of 5 mg/ml, then mixed solution was incubated for 40 minutes after which the solution was centrifuged and the supernatant was analyzed using BPLC.

Loading Efficiency

Loading efficiency is the ratio between MPS/phospholipid concentrations after and before loading. The quantification of MPS was done in an HPLC apparatus as described by Anderson, and Taphouse 1981 [Anderson B. D. and Taphouse. V. J *Pharm Sci*, 70:181-6 (1981)], quantification of phospholipid was done by modified Bartlet procedure [Shmeeda, H., et al. In: Methods in Enzymology "Liposomes", (Düzgünes, N., ed.), 367:272-292 (2003)].

Stability Determination

Determination of MPS Release from Liposome

The level of MPS released from SSL-MPS was determined by first separating the liposomes from free MPS using gel exclusion chromatography on Sepharose cross-linked CL-4B column using. Liposomes were eluted at the void volume and the free MPS at the later eluted fractions (FIG. 3A-3B).

Stability upon storage at 4° C. and kinetic of release at 37° C. in 80% plasma was determined by gel exclusion chromatography described above. Then the different column fractions were analyzed as described above, for MPS, phospholipids and Ca in the void volume fraction.

In addition, SSL-MPS were incubated with 80% human inflamed synovial fluid at a ratio of 80% plasma at 37° C. Then at different time points sample were vortexed with the anion exchange resin, DOWEX 1×400 mesh (C$^-$ form), which bind only free MPS. The samples were analyzed for liposome encapsulated MPS and liposome phospholipid content.

Results

Table 1 below provides logD and pKa of the tested GC derivatives, as calculated using Advanced Chemistry Development (ACD/Labs) [Software Solaris V4.67 ( 1994-2005 ACD/Labs) SciFinder SCHOLAR Version 2004.2 © American Chemical Society 2004].

TABLE 1 logD and pKa of some acidified GC

| pKa | logD at pH 7 | Modified GC |
|---|---|---|
| 1.67 ± 0.10 | −4.25 | Prednisolone phosphate |
| 4.29 ± 0.17 | −0.64 | Prednisolone hemisuccinate |
| 1.67 ± 0.10 | −3.76 | Methylprednisolone phosphate |
| 4.29 ± 0.17 | −0.15 | Methylprednisolone hemisuccinate |
| 1.67 ± 0.10 | −3.88 | Dexamethasone phosphate |
| 4.29 ± 0.17 | −0.27 | Dexamethasone hemisuccinate |

Turbidity, Partition Coefficient and Surface Tension of MPS

The turbidity (indicating the aggregation) of MPS was determined. The results shown in FIG. 1A indicate that at pH 7.2 the amphipathic weak acid derivative (the pro-drug) is non-aggregated water soluble and in acidic pH, it aggregates, therefore showing increase in turbidity. The decline in turbidity observed at very low pH, was due to the formation of very large aggregates which precipitated. The doted arrow indicates the point of transition from titration with HCl (µmol of H$^+$, left side of arrow) to titration with NaOH (µmol of OH$^-$, right side of arrow).

Figure 1B:
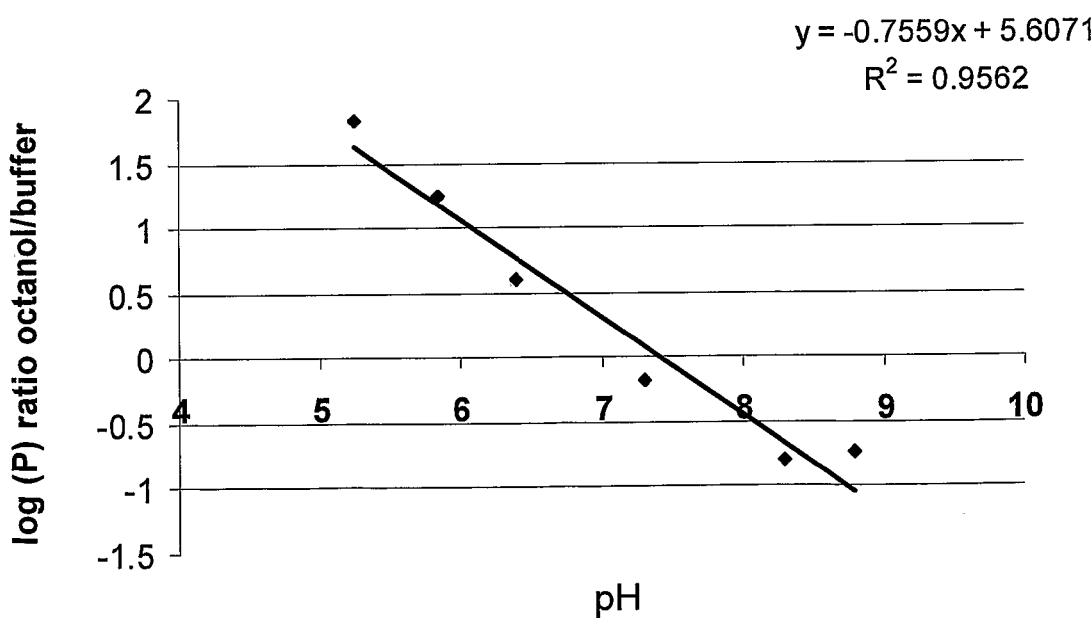
Figure 1C:
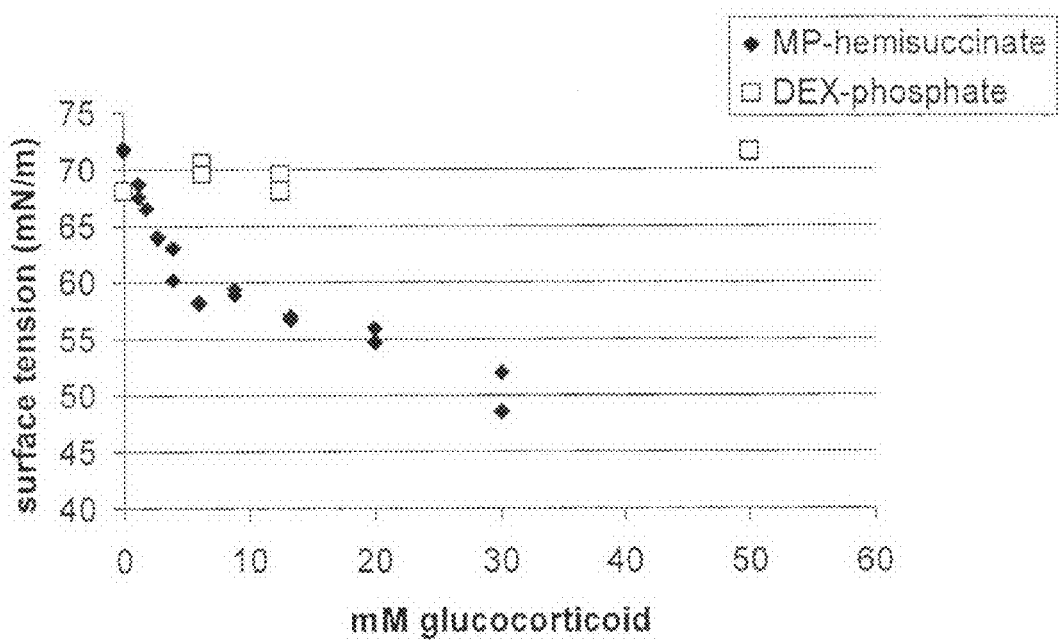

Partition coefficient of MPS was determined at different pH points. As shown in FIG. 1B, MPS is indeed an amphipathic substance.

Further, the surface tension of MPS was determined and as evident from FIG. 3C, MPS is surface active at all concentrations used (0.785-30 mM) and has a CAC (critical association/aggregation concentration) point at ~5 mM while GC that has a phosphate group (a strong acidic group) such as dexamethasone phosphate was not surface active at least up to concentration of 50 mM and did not self associated to form micelles and/or other organized assemblies.

Precipitation of MPS by Calcium Ion

The precipitation of MPS in the presence of calcium acetate solution was determined as described above. Table 2 shows the percent of MPS that precipitated in the presence of calcium ions, i.e. at different pH. As shown, precipitation already occurred at pH 6.8. Precipitation was increased to a very large extent (97% of the MPS) at pH around the pKa of GC (pH 4.5).

TABLE 2 precipitation of MPS

| % MPS precipitated | pH |
|---|---|
| 44.1 | 6.8 |
| 42.8 | 6.2 |
| 96.6 | 4.5 |

General Loading Efficiency for Different Liposomal Formulations

1. Liposome Loading Efficiency

Three separate batches (identified by dates) were used in order to determine loading efficacy of the drug into the liposomes (HSPC:Chol:$^{2000}$PEG-DSPE (54:41:5 mole ratio)), as summarized in Table 3.

TABLE 3

Loading efficacy into liposome

| % Encapsulation | MPS/lipid (mg/μmole) | mM phosphate | mg/ml MPS | 18 Jul. 2004 |
|---|---|---|---|---|
|  | 0.188 | 39.80 | 7.46 | Before dialysis[a] |
| 99.1 | 0.186 | 40.70 | 7.56 | After dialysis[b] |

| % Encapsulation | MPS/lipid (mg/μmole) | mM phosphate | mg/ml MPS | 06 Apr. 2005 |
|---|---|---|---|---|
|  | 0.19 | 33.20 | 6.22 | Before dialysis[a] |
| 96.6 | 0.18 | 27.60 | 4.99 | After dialysis[b] |

| % Encapsulation | MPS/lipid (mg/μmole) | mM phosphate | mg/ml MPS | 04 May 2005 |
|---|---|---|---|---|
|  | 0.21 | 45.73 | 9.68 | Before dialysis[a] |
| 93.2 | 0.20 | 32.19 | 6.35 | After dialysis[b] |

[a] MPS in liposome + MPS in the extraliposome medium
[b] MPS in liposome only

2. Loading Efficiency of MPS for Different Liposomal Formulations

It was determined that the optimum conditions for efficient loading include ~600 mOsm of Calcium acetate. The loading efficiency of MPS in HSPC:Chol:$^{2000}$PEG-DSPE (55:40:5 mole ratio) liposomes with this MPS/phospholipids ratio was obtained when using initial pro-drug concentration between 5-10 mg/ml, preferably 9 mg/ml. The concentration of the pro-drug in the final formulation was ~6.5 mg/ml which was used in the following experiments (hereinafter termed the SSL-MPS formulation or in brief SSL-MPS).

Figure 2A:
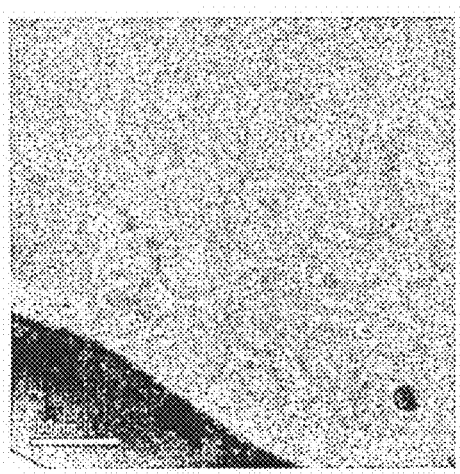
FIGS. 2A-2B—are Cryo-TEM (transmission electron microscopy) images of liposomes before (FIG. 2A) and after (FIG. 2B) active loading of MPS.
Figure 2B:
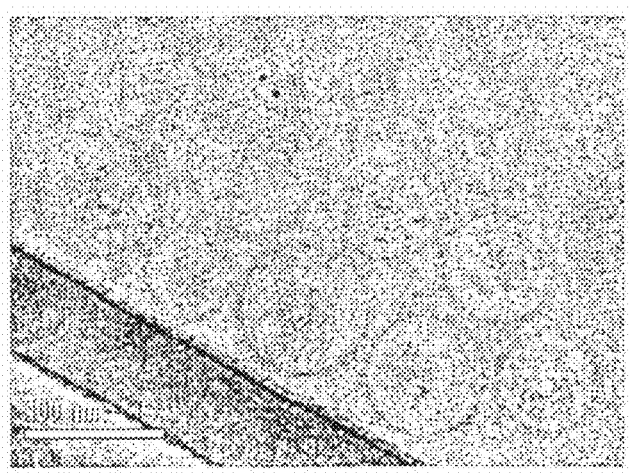

FIG. 2A-2B are Cryo-TEM images of liposomes before (FIG. 2A) and after (FIG. 2B) loading clearly showing location of the precipitate in the internal aqueous space of the liposome.

Stability of Liposomal Formulation

The concentration of MPS in SSL-MPS (i.e. intact liposomal formulation) over 14 months was determined as described above. FIG. 3A shows that after 14 months ~80% of MPS was retained in the liposome. Part of the free MPS was hydrolyzed to its active form, methylrednisolone (MP). FIG. 3B provides a Sepharose 4B size-exclusion chromatograph of the liposomal preparation at after 14 months of storage at 4° C., with an enlargement (FIG. 3C) of the graph at fractions 8 to 17, showing the existence of free MPS as well as free MP.

Figure 4A:
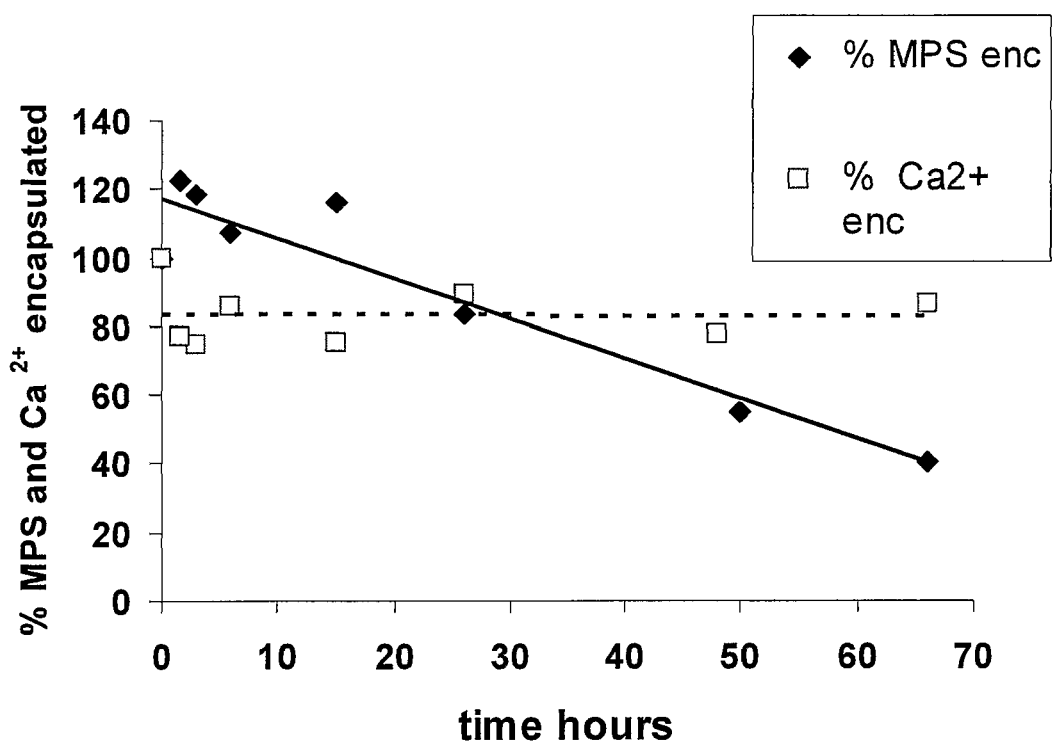
FIG. 4A-4B are release profiles of MPS and $Ca^{+2}$ from SSL-MPS when incubated at 37° C. in plasma (FIG. 4A) or in inflamed synovial fluid (FIG. 4B).
Figure 4B:
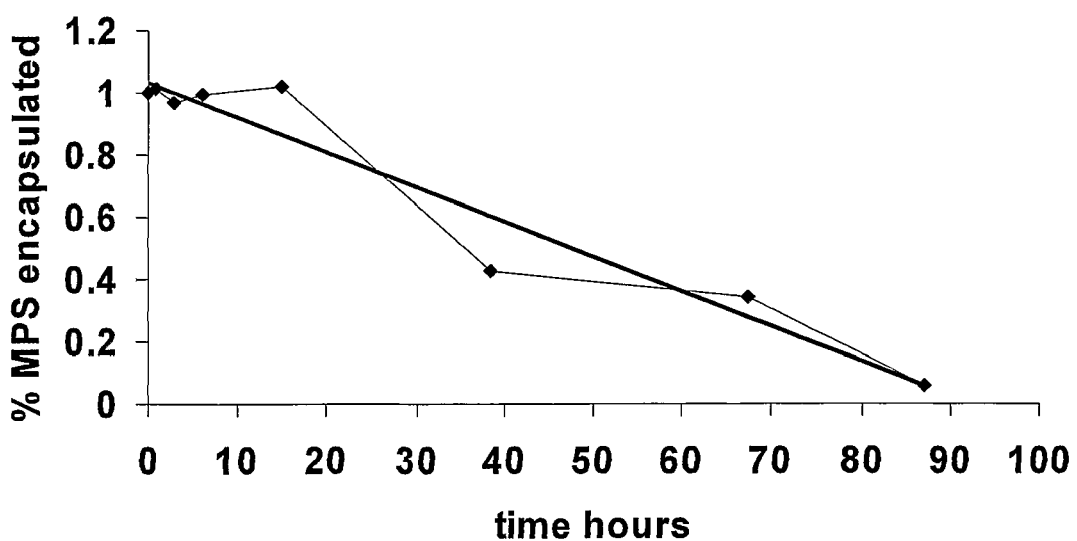

Further, stability of SSL-MPS in clinical relevant milieus was determined. FIGS. 4A-4B show the stability of the liposomal formulation in human plasma and inflamed synovial fluid. The retention of 100% of the encapsulated calcium in the encapsulated liposome under condition that MPS is released (with a half life in liposome of 50 hours) indicates that the liposomes are intact for at least 66 hours in plasma. This suggests that the release of MPS is due to its amphiphacy. The half life of MPS release is in a similar value to SSL half life in plasma post i.v. injection.

Rheumatic Arthritis Modeled by Adjuvant Arthritis

Adjuvant Arthritis (AA) Induction

Female inbred 6-week old Lewis rats (Harlan labs. Israel) were injected s.c. at the base of the tail with 1 mg of *Mycobacterium* Tuberculosis H37Ra (MT) in CFA. Severity of arthritis (AA score) was assessed every other day as fellows: 0=no arthritis; 1=redness of the joint; 2=redness and swelling of the joint. The ankle and tarsal-metatarsal joints of each paw were scored.

Tissue Distribution

In order to estimate the ability of SSL to extravasate selectively into inflamed tissues SSL-MPS clearance from plasma and tissue in healthy and arthritic rats was determined. Specifically, SSL-MPS was injected into healthy and arthritic Lewis rats 22 days after injection of FCA (maximum swelling) at a dose of Phospholipid concentration of 42 mg/kg (56 μmol/kg). At 4 time points after injection: 4, 24, 48, and 72 h, the rats were sacrificed and their plasma, liver, kidneys, spleen, and lungs were tested for liposomal marker [$^3$H] cholesteryl hexadeyl ether (in whole tissue) using a Sample Oxidiser (Model 307, Packard Instrument Co., Meriden, Conn.), for radioactivity measurements in the Sample Oxidizer. All tissues were oxidized as is, without homogenization. The limitation of this method is that the weight per sample should not exceed 0.5 g, therefore skin and joints were divided into pieces (≦0.5 g) and their [$^3$H] cholesteryl ether level was determined by the Sample Oxidizer.

Figure 5:
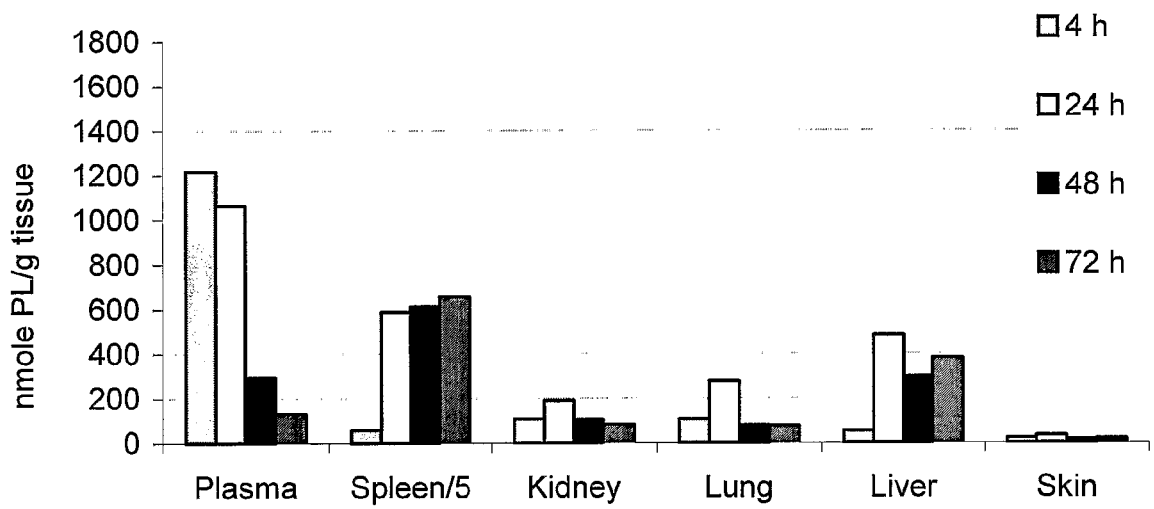
FIG. 5 is a bar graph showing the bio-distribution of SSL-MPS in the body including in plasma, spleen (value divided by 5), kidney, lung, liver and skin at different time points.

A slow clearance rate of the SSL was observed in both healthy and arthritic rats, with a similar $t_{1/2}$ of 23 h in healthy and 25 h in arthritic rats, as was calculated using WinNolin analytical software. Seventy nine percent and 81% of the injected SSL-MPS dose stayed in plasma 4 h after the injection in arthritic and healthy rat accordingly. Table 4A-4B and FIG. 5A-5B, present quantitative bio-distribution data which show that similar amounts of the liposome were found in tissues isolated from healthy (Table 2A, FIG. 5A) and arthritic rats (Table 2B, FIG. 5B).

TABLE 4A

Bio-distribution in healthy rats
Percent of injected dose (% ID)

| SSL after 24 hours | SSL after 4 hours | Organs |
|---|---|---|
| 54 | 79 | Plasma |
| 10 | 2.4 | Liver |
| 1.7 | 0.43 | Lung |
| 5 | 0.7 | Spleen |
| 2.5 | 1 | Kidney |
| 73.2 | 83.5 | Total |

TABLE 4B

Bio-distribution in AA rats
Percent of injected dose (% ID)

| SSL- after 24 hours | SSL- after 4 hours | Organs |
|---|---|---|
| 58 | 81 | Plasma |
| 9.50 | 2.35 | Liver |
| 0.80 | 0.67 | Lung |
| 2.80 | 0.75 | Spleen |
| 1.25 | 0.7 | Kidney |
| 72.35 | 85.54 | Total |

Figure 6:
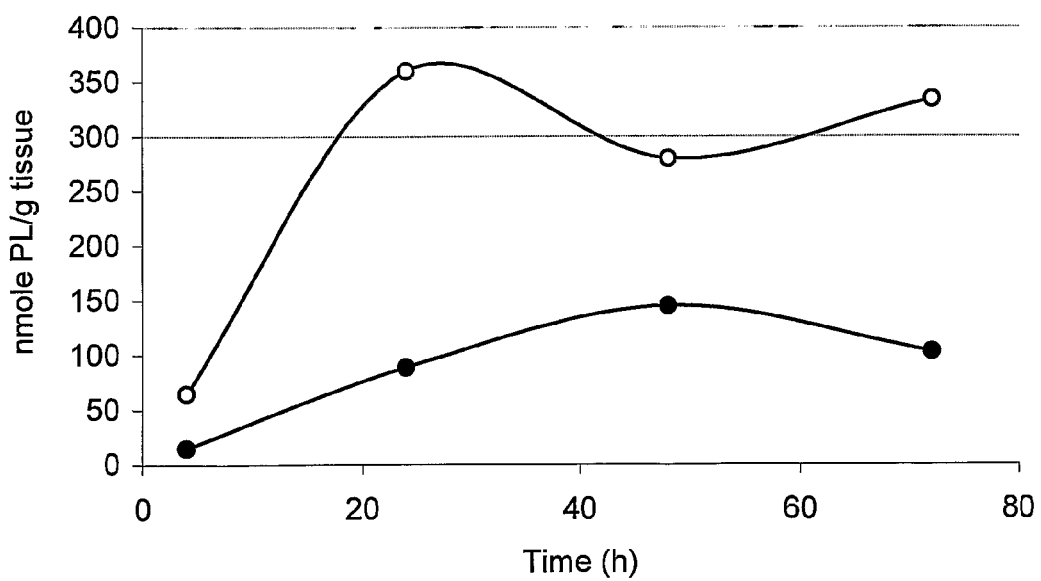
FIG. 6 is a graph showing SSL-MPS distribution into a non arthritic (●) and an arthritic rat paw (○).

Comparing arthritic and healthy rats it was shown that significantly (2 to 4-fold) higher extravasation of SSL-MPS into the inflamed paws of arthritic rats was observed at all time-points compared to the non-inflamed paws of healthy rats (FIG. 6). SSL-MPS concentration in the inflamed paws remained roughly unchanged from 24 h to at least 72 h ($\approx$220 µg lipid/g tissue; 293 µmole lipid/g tissue; 7% ID/paw). SSL-MPS concentration in the paws of healthy rats was maximal at 48 h (100 µg/g tissue or only 2% ID/paw). 16-fold higher approximate AUC value of the inflamed paw was obtained compared to approximate AUC value of the healthy paw 3000 (h×µg/g tissue) compared to 4600 (h×µg/g tissue) (as was calculated using WinNonlin analytical software; approximate values were used because no decline in SSL concentrations was observed at 72 h post-injection).

Treatment of AA by Liposome-targeted Methylprednisolone Succinate Sodium Salt (SSL-MPS).

Evaluation of the effect of SSL-MPS on AA was determined in two successive assays:

(1) Lewis rats were treated with 2 i.v. injections (on days 10 and 14 after AA induction) of free MPS and SSL-MPS. The first injection of both formulations was 5 mg/kg body weight (BW) and the second was 10 mg/kg BW. Control rats were treated with empty SSL or PBS.

(2) Lewis rats were treated with 2 injections of free MPS (10 and 50 mg/kg per body weight), or SSL-MPS (0.4, 2, and 10 mg/kg BW). Control rats were treated with PBS. An additional group of rats received 3 i.v. injections (on days 10, 14 and 18 after AA induction) of 10 mg/kg BW SSL-MPS.

(3) In an alternative assay, for determining effect of SSL-MPS at peak of disease Lewis rats were treated with one of the following: dextrose 5% (on days 19, 23); free-MPS 10 mg/kg BW (on days 19, 23); SSL-MPS 10 mg/kg BW (on days 19, 23) and as a positive control, with Remicade 5 mg/kg (on day 19).

Modulation of AA by SSL-MPS Treatment

The therapeutic effect of the SSL-MPS on AA was tested by treating AA-induced rats with 2 i.v. injections on days 10 and 14 after disease induction as described above. The first injection was 5 mg/kg BW and the second-10 mg/kg BW. Control rats were treated with the free MPS, with empty liposome or with PBS.

Figure 7A:
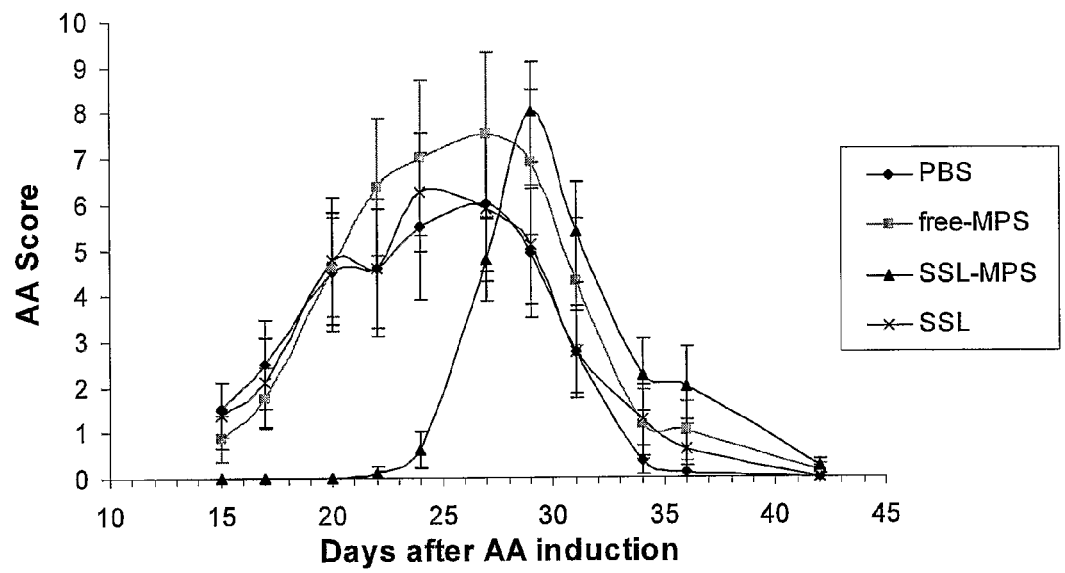
FIG. 7A-7B are graphs showing the effect of free MPS (10 and 50 mg/kg body weight, "Ster. 10" or "Ster. 50", respectively), SSL-MPS (10, 2 and 0.4 mg/kg bw, "Lip. 10", "Lip. 2", "Lip. 0.4", respectively) on Adjuvant Arthritis (AA) induced animals, following two different treatment regimes as described below.

As can be seen in FIG. 7A, neither the free MPS nor the empty liposome had any effect on AA. However, a significant delay of disease onset was found in rats treated with SSL-MPS. The first signs of disease become apparent only after 10 days from the second injection (day 24) and even on day 26 there was still a significant lower severity of the disease compared with the disease state in free MPS or PBS treated rats.

To further assess the efficacy of this treatment rats were treated with 2 i.v. injections (on days 10 and 14 as above) of 10 mg/kg BW and with a 5-fold higher concentration of the steroid (i.e. 50 mg/kg BW) as well as with 5-fold lower concentrations of the SSL-MPS (i.e. 10, 2 and 0.4 mg/kg BW). Control rats received PBS. Another group of rats received a third injection (on day 18) of SSL-MPS at a dose of 10 mg/kg BW.

Figure 7B:
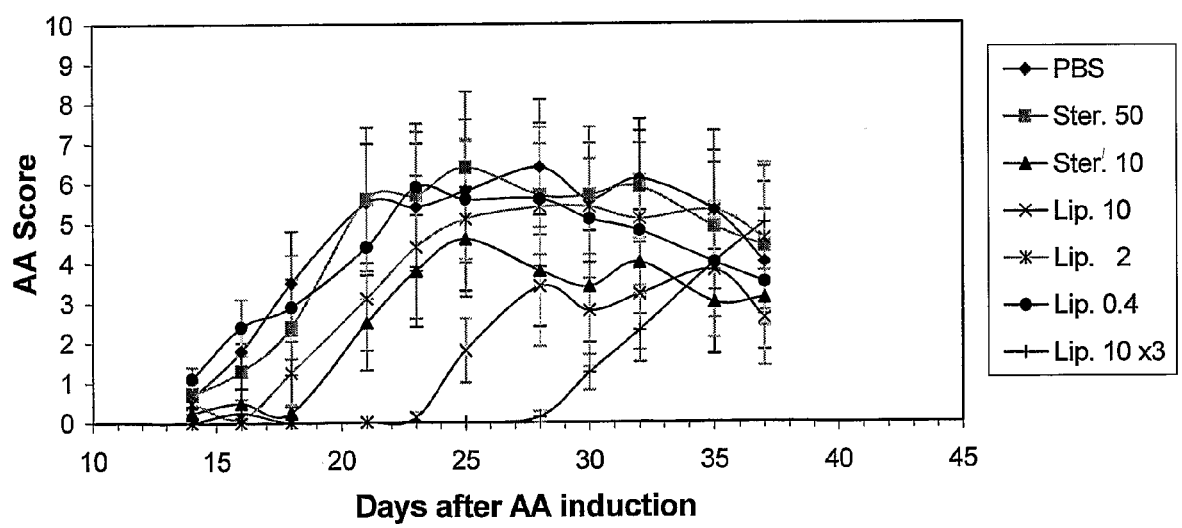

FIG. 7B shows that 2 injections of SSL-MPS (10 mg/kg BW) delayed the onset of disease for more than 10 days and also decreased the peak arthritic-score of the liposome-treated rats in comparison to PBS-treated rats. The third injection caused a further delay of extra 10-11 days in the onset of AA. In these rats the disease peaked when PBS-treated rats were already in the recovery phase. The two lower doses of the SSL-MPS (0.4 mg/kg BW) was less effective while 2 mg/kg showed only small effect. Namely, this experiment showed a dose response curve for SSL-MPS.

Effect of SSL-MPS at Peak of Disease

AA induced rats were treated as described above. Immediately after injection of SSL-MPS a sharp decline in the clinical score for the SSL-MPS treated group was observed while the other groups (dextrose 5%, free-MPS, empty SSL, REMICADE) showed a very slow decline, similar to that observed with the control (dextrose) group.

The second injection at day 23 caused a further decline in AA score while the other groups (dextrose 5%, free-MPS, empty SSL and REMICADE) showed a minimal decline, again, similar to that of the control (dextrose) group.

Yet, at day 30 the score of the SSL-MPS group started to rise, and at day 47 a decline of disease, in line corresponding to that of other groups was observed.

Figure 8:
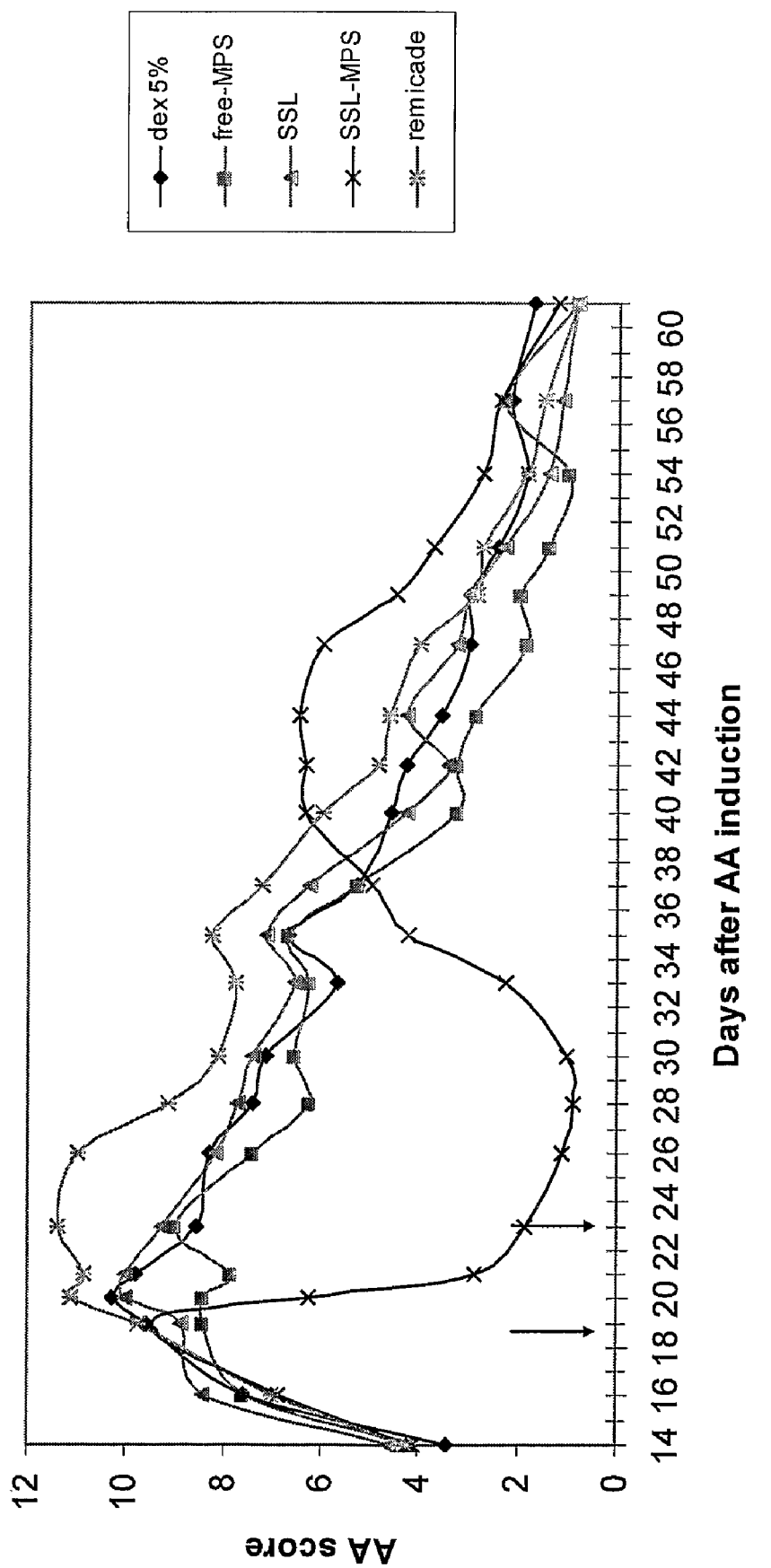
FIG. 8 is a graph showing the effect of SSL-MPS treatment on AA at peak of disease.

The results which are also shown in FIG. 8 indicate that SSL-MPS has a beneficial therapeutic effect at peak of inflammatory state which is greater than that of Remicade and free-MPS.

The invention claimed is:

1. A method for the treatment of an inflammatory associated condition in a subject, provided that the condition is not associated with a neurodegenerative disease or disorder, the method comprises administering to the subject in need thereof an amount of a GC or GC derivative encapsulated in a liposome and essentially retained in the liposome for 6 months under storage conditions at 4° C., wherein the liposome comprises a lipopolymer and liposome forming lipids, the amount of the GC or GC derivative being effective to treat the inflammatory associated condition, wherein the GC or GC derivative is selected from the group consisting of:

i) an amphipathic weak base GC or GC derivative having a pKa equal or below 11 and a logD at pH 7 in the range between about −2.5 and about 1.5; and ii) an amphipathic weak acid GC or GC derivative having a pKa above 3.5 and a logD at pH 7 in the range between about −2.5 and about 1.5 wherein at least inflammation is treated.

2. The method of claim 1, wherein the liposome has a mole ratio between the GC or GC derivative and the lipid of between 0.01 and 2.0.

3. The method of claim 1, wherein the liposome forming lipid comprises a glycerol backbone wherein at least one of the hydroxyl groups at the head groups is substituted with an acyl chain, or the liposome forming lipid is a sphingolipid.

4. The method of claim 1, wherein the GC or GC derivative is selected from an amphipathic weak base having a pKa or below 11 and a logD at pH 7 in the range between −1.5 and 1.0, or an amphipathic weak acid GC or GC derivative having a pKa above 3.5 and a logD at pH 7 in the range between −1.5 and 1.0.

5. The method of claim 1, comprising administering to the subject a GC derivative which is converted to an active GC upon release thereof from the liposome into a body fluid.

6. The method of claim 1, wherein the GC or GC derivative is an acidic GC or GC derivative.

7. The method of claim 6, wherein the acidic GC is a GC derivative selected from methylprednisolone sodium hemisuccinate (MPS), hydrocortisone sodium hemisuccinate (HYD), Dexamethasone hemisuccinate, and Prednisolone hemisuccinate.

8. The method of claim 1, wherein the liposome forming lipids comprise a phospholipid.

9. The method of claim 8, wherein the liposome comprises a combination of a phospholipid, a lipopolymer and cholesterol.

10. The method of claim 8, wherein the liposome comprises a combination of hydrogenated soybean phosphatidylcholine (HSPC), polyethylene glycol coated distearoyl phosphatidyl ethanolamine (PEG-ESPE) and cholesterol.

11. The method of claim 1, wherein the liposome is a sterically stabilized liposome (SSL).

12. The method of claim 1, wherein the liposome comprises a mole ratio between the GC or GC derivative and the lipid of between 0.04 and 0.25.

13. The method of claim 1, wherein inflammation is caused by an autoimmune disorder.

14. The method of claim 13, wherein the autoimmune disorder is arthritis (RA).

15. The method of claim 1, wherein the administration is by parenteral administration, oral administration or intranasal administration of the liposomes encapsulating GC or GC derivative.

16. The method of claim 15, wherein the parenteral administration is by infusion or injection.

* * * * *